(12) United States Patent
Gordon et al.

(10) Patent No.: US 10,762,429 B2
(45) Date of Patent: Sep. 1, 2020

(54) EMOTIONAL/COGNITIVE STATE PRESENTATION

(71) Applicant: Microsoft Technology Licensing, LLC, Redmond, WA (US)

(72) Inventors: John C. Gordon, Newcastle, WA (US); Cem Keskin, Seattle, WA (US)

(73) Assignee: Microsoft Technology Licensing, LLC, Redmond, WA (US)

( * ) Notice: Subject to any disclaimer, the term of this patent is extended or adjusted under 35 U.S.C. 154(b) by 871 days.

(21) Appl. No.: 15/158,409

(22) Filed: May 18, 2016

(65) Prior Publication Data

US 2017/0337476 A1 Nov. 23, 2017

(51) Int. Cl.
| | |
|---|---|
| *G06N 5/02* | (2006.01) |
| *G06F 3/01* | (2006.01) |
| *A61B 5/16* | (2006.01) |
| *H04N 21/4223* | (2011.01) |
| *G06K 9/00* | (2006.01) |
| *H04N 21/845* | (2011.01) |
| *H04N 21/433* | (2011.01) |
| *H04N 21/4363* | (2011.01) |
| *H04N 21/442* | (2011.01) |

(Continued)

(52) U.S. Cl.
CPC ............. *G06N 5/022* (2013.01); *A61B 5/165* (2013.01); *G06F 3/011* (2013.01); *G06F 3/013* (2013.01); *G06F 3/015* (2013.01); *G06F 3/017* (2013.01); *G06K 9/00302* (2013.01); *G06K 9/00671* (2013.01); *G06T 19/006* (2013.01); *H04N 21/4223* (2013.01); *H04N 21/42201* (2013.01); *H04N 21/42202* (2013.01); *H04N 21/4334* (2013.01); *H04N 21/43637* (2013.01); *H04N 21/44231* (2013.01); *H04N 21/8456* (2013.01); *A61B 5/0205* (2013.01); *G06F 1/1613* (2013.01); *G06F 2203/011* (2013.01); *G06K 9/00597* (2013.01); *G06T 2219/012* (2013.01)

(58) Field of Classification Search
None
See application file for complete search history.

(56) References Cited

U.S. PATENT DOCUMENTS

| | | |
|---|---|---|
| 6,558,050 B1 | 5/2003 | Ishibashi |
| 8,368,794 B2 | 2/2013 | Sako et al. |

(Continued)

FOREIGN PATENT DOCUMENTS

| | | |
|---|---|---|
| EP | 1422639 A2 | 5/2004 |
| EP | 1879384 A1 | 1/2008 |

OTHER PUBLICATIONS

"Non-Final Office Action Issued in U.S. Appl. No. 15/158,439", dated May 19, 2017, 11 Pages.

(Continued)

*Primary Examiner* — George Giroux
(74) *Attorney, Agent, or Firm* — Newport IP, LLC; Jacob P. Rohwer

(57) ABSTRACT

Emotional/cognitive state presentation is described. When two or more users, each using a device configured to present emotional/cognitive state data, are in proximity to one another, each device communicates an emotional/cognitive state of the user of the device to another device. Upon receiving data indicating an emotional/cognitive state of another user, an indication of the emotional/cognitive state of the user is presented.

18 Claims, 18 Drawing Sheets

(51) Int. Cl.
*G06T 19/00* (2011.01)
*G06F 1/16* (2006.01)
*H04N 21/422* (2011.01)
*A61B 5/0205* (2006.01)

(56) References Cited

U.S. PATENT DOCUMENTS

| | | | |
|---|---|---|---|
| 8,441,356 B1 | 5/2013 | Tedesco et al. | |
| 9,183,761 B1* | 11/2015 | Ciechanowski | G09B 23/28 |
| 9,311,825 B2* | 4/2016 | Lusted | G09B 19/00 |
| 10,154,191 B2 | 12/2018 | Gordon et al. | |
| 2004/0101178 A1 | 5/2004 | Fedorovskaya et al. | |
| 2005/0174470 A1 | 8/2005 | Yamasaki | |
| 2009/0157672 A1* | 6/2009 | Vemuri | G09B 19/00 |
| 2010/0086204 A1 | 4/2010 | Lessing | |
| 2010/0306655 A1* | 12/2010 | Mattingly | G06Q 10/10 |
| | | | 715/720 |
| 2011/0179003 A1* | 7/2011 | Min | H04N 21/278 |
| | | | 707/706 |
| 2013/0133026 A1* | 5/2013 | Burgess | G06F 21/62 |
| | | | 726/1 |
| 2013/0177296 A1 | 7/2013 | Geisner et al. | |
| 2013/0278620 A1 | 10/2013 | Jow et al. | |
| 2014/0006326 A1* | 1/2014 | Bazanov | G06Q 10/103 |
| | | | 706/46 |
| 2014/0012785 A1* | 1/2014 | Kim | G06N 5/025 |
| | | | 706/12 |
| 2014/0089399 A1* | 3/2014 | Chun | G06Q 50/01 |
| | | | 709/204 |
| 2014/0204119 A1* | 7/2014 | Malamud | G06T 19/006 |
| | | | 345/633 |
| 2014/0221866 A1 | 8/2014 | Quy | |
| 2015/0178915 A1* | 6/2015 | Chatterjee | G06F 16/58 |
| | | | 382/128 |
| 2015/0187083 A1 | 7/2015 | Yoon et al. | |
| 2015/0281783 A1* | 10/2015 | Laksono | H04N 21/4415 |
| | | | 725/10 |
| 2015/0371015 A1* | 12/2015 | Garcia Manchado | H04L 63/04 |
| | | | 726/30 |
| 2016/0073947 A1 | 3/2016 | Anderson | |
| 2016/0221502 A1* | 8/2016 | Gordon | G06K 9/00845 |
| 2019/0075239 A1 | 3/2019 | Gordon et al. | |

OTHER PUBLICATIONS

"Non-Final Office Action Issued in U.S. Appl. No. 15/158,439", dated Mar. 8, 2018, 13 Pages.

"International Search Report and Written Opinion Issued in PCT Application No. PCT/US2017/032306", dated Sep. 13, 2017, 19 Pages.

Healey, et at, "StartleCam: A Cybernetic Wearable Camera", In Proceedings of the Second International Symposium on Wearable Computers, Oct. 19, 1998, 8 Pages.

"International Search Report and Written Opinion Issued in PCT Application No. PCT/US2017/031841", dated Aug. 11, 2017, 16 Pages.

U.S. Appl. No. 15/158,439—Final Office Action, dated Oct. 13, 2017, 12 Pages.

"Non Final Office Action Issued in U.S. Appl. No. 16/183,609", dated Mar. 21, 2019, 7 Pages.

* cited by examiner

EMOTIONAL/COGNITIVE STATE PRESENTATION

BACKGROUND

Digital media has made it increasingly easy for people to record, through photos and videos, meaningful moments throughout their lives. However, oftentimes, a meaningful moment has already begun before a user realizes that it is a moment they would like to capture. Furthermore, users are often so focused on wanting to capture important moments that they spend more time trying to capture a photo or video instead of enjoying the moment.

Furthermore, while social media applications have made it easy for users to share their emotions with others (e.g., posting an emoticon to in response to another user's post), the prevalence of social and digital media has done little to improve face-to-face user interactions.

SUMMARY

This disclosure describes techniques for emotional/cognitive state-triggered recording. In an example, one or more sensors gather sensor data while a camera captures video content to a buffer. Based on the sensor data, an emotional or cognitive state of a user is determined. Upon detecting a change in the emotional/cognitive state of the user, a video segment is created based on the video content currently in the buffer. Additional video content may be captured and added to the video segment, for example, until another change in the emotional or cognitive state of the user is detected. In this way, video segments are created, which correspond to periods of time during which a user experienced a change in an emotional or cognitive state. For example, while watching a child's sporting event, if the child scores a point, causing the user (the parent) to get excited, happy, or proud, a video segment will be created and stored that includes a few minutes prior to and after the child scored the point.

This disclosure also describes an emotional/cognitive state presentation system, which enables users to dynamically and automatically share their emotional or cognitive state with another user using an electronic device. For example, two users with a trusted relationship, may each be using a device configured to enable emotional/cognitive state presentation. Sensor data may be gathered in association with each user, which is used to determine a current emotional or cognitive state of the respective user. The data is then shared and presented, enabling each user to be aware of the other user's current emotional or cognitive state.

This Summary is provided to introduce a selection of concepts in a simplified form that are further described below in the Detailed Description. This Summary is not intended to identify key or essential features of the claimed subject matter, nor is it intended to be used as an aid in determining the scope of the claimed subject matter. The term "techniques," for instance, may refer to system(s), method(s), computer-readable instructions, module(s), algorithms, hardware logic, and/or operation(s) as permitted by the context described above and throughout the document.

BRIEF DESCRIPTION OF THE DRAWINGS

The detailed description is described with reference to the accompanying figures. In the figures, the left-most digit(s) of a reference number identifies the figure in which the reference number first appears. The same reference numbers in different figures indicate similar or identical items.

DETAILED DESCRIPTION

Overview

Techniques for emotional/cognitive state-triggered recording are described herein. In an example implementation described herein, a wearable camera continuously records video to a buffer. Any number of various types of sensors can be used to determine an emotional or cognitive state of a user. Upon detecting a particular emotional or cognitive state, or upon detecting a degree of an emotional or cognitive state that exceeds a threshold, the contents of the buffer and additional recorded video content is saved as a video segment corresponding to a moment that is meaningful to the user. As used herein, emotional states may include, but are not limited to, happiness, sadness, anger, fear, disappointment, or pride. Similarly, cognitive states may include, but are not limited to, focused, engaged, distracted, bored, sleepy, confused, or frustrated.

Techniques for emotional/cognitive state presentation are also described herein. In an example implementation, individuals with devices configured to present emotional/cognitive state can interact with one another such that each user's current emotional/cognitive state is presented to the other user. Any number of various types of sensors can be used to determine an emotional or cognitive state of a user.

If another user is in proximity and using a device that is also configured to present the emotional/cognitive state of the user, the devices of each user enable the emotional/cognitive state of the respective user to be presented to the other user. In an example implementation, the emotional/cognitive state of the other user is presented as an aura around the user within an augmented reality, which is viewed, for example, through a head-mounted display device.

Emotional/Cognitive State-Triggered Recording

Figure 1:
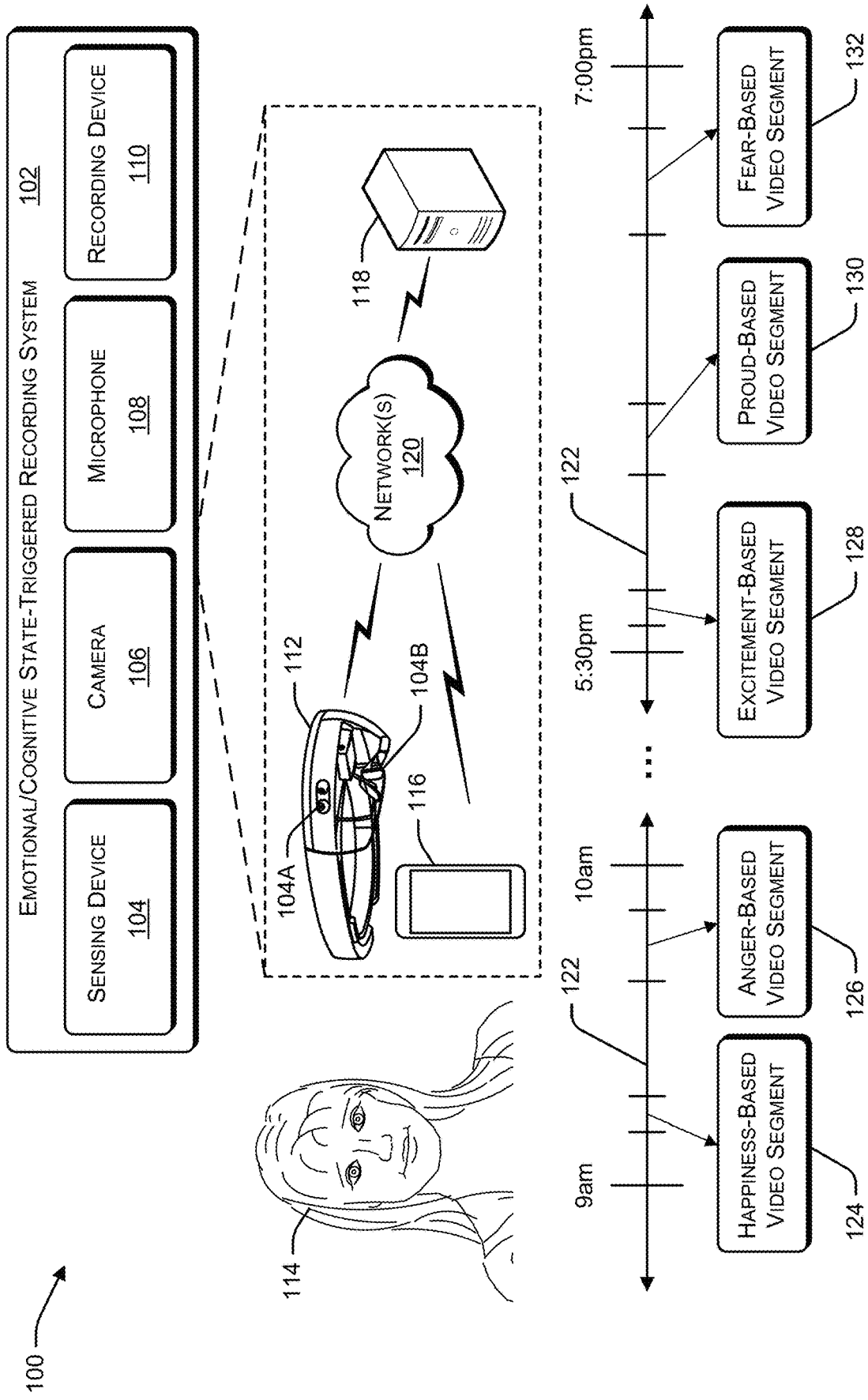
FIG. 1 is a pictorial diagram illustrating an example environment in which an emotional/cognitive state-triggered recording system can be implemented.

FIG. 1 illustrates an example environment 100 in which emotional/cognitive state-triggered recording can be implemented. Example environment 100 includes emotional/cognitive state-triggered recording system 102, which includes a sensing device 104, a camera 106, a microphone 108, and a recording device 110. In an example implementation, any combination of sensing device 104, camera 106, microphone 108, and recording device 110 may be implemented as a single device. For example, sensing device 104, camera 106, microphone 108, and recording device 110 may be implemented as a single, wearable device, such as head-mounted display (HMD) device 112.

In another example, sensing device 104, camera 106, microphone 108, and/or recording device 110 may be implemented as a plurality of devices. For example sensing device 104 may be implemented as one or more devices, one or more of which may be worn or carried by the user 114. For example, sensors may be components of HMD device 112, cell phone 116, and any number of other devices. As another example, camera 106 and microphone 108 may be implemented as a component of a device worn or carried by the user 114. For example, camera 106 and microphone 108 may be components of HMD device 112 or cell phone 116. As yet another example, recording device 110 may be implemented as any combination of components of HMD device 112, cell phone 116, and/or computing device 118. For example, sensing device 104, camera 106, and microphone 108 may be communicatively connected to recording device 110. Any combination of HMD device 112, cell phone 116, and computing device 118 may communicate with one another via, for example, Bluetooth or other short-range wireless communication protocol, or via a network 120.

In at least one example, the sensing device 104 can be any device or combination of devices configured to physiologically monitor a user 114. Individual sensors of one or more sensing devices 104 can include, but are not limited to, a galvanic skin response sensor for measuring galvanic skin response, a skin temperature sensor for measuring the temperature on the surface of the skin, an electroencephalography (EEG) device for measuring electrical activity of the brain, an electrocardiography (ECG or EKG) device for measuring electrical activity of the heart, cameras for tracking eye movement, facial expressions, pupil dilation and/or contraction, etc., sound sensors for measuring a volume of speech, a rate of speech, etc. In an example implementation, the sensor data can include measurements associated with a physiological attribute of a user 114, which can be an indicator of an emotional or cognitive state.

In an example, the sensing device 104 is part of, or built into, a particular device. For example, as illustrated in FIG. 1, HMD device 112 may include a camera sensor 104A and a galvanic skin response sensor 104B associated with a nose-bridge component of the HMD device 112.

A user of emotional/cognitive state-triggered recording system 102 may activate the system to capture video segments based on detected emotional/cognitive states of the user, for example, via a user interface or a hardware switch. In the example illustrated in FIG. 1, timeline 122 represents user activities in an example day. In the illustrated example, the user attends a work meeting between 9:00 am and 10:00 am and attends her son's baseball game between 5:30 pm and 7:00 pm. At approximately 9:10 am, a co-worker announces that all company employees will be receiving a bonus next week. This announcement evokes feelings of happiness for the user, triggering emotional/cognitive state-triggered recording system 102 to record a happiness-based video segment 124. Later during the same meeting, a heated discussion about an error that was made in processing a customer order evokes feelings of anger for the user. The emotional/cognitive state-triggered recording system 102 detects the user's anger, and in response, records an anger-based video segment 126.

At 5:30, the user attends her son's baseball game. The user gets excited when her son is first up to bat. The emotional/cognitive state-triggered recording system 102 detects the user's excitement, and in response, records an excitement-based video segment 128. Later in the game, the user's son hits a homerun, causing the user to feel proud of her son. The emotional/cognitive state-triggered recording system 102 detects the user's feelings of pride, and in response, records a proud-based video segment 130. Still later in the game, the user's son collides with another player and falls to the ground, obviously in pain. This scenario evokes feelings of fear in the user. The emotional/cognitive state-triggered recording system 102 detects the user's fear, and in response, records a fear-based video segment 132.

At the end of the day, the user is able to review the various video segments that were recorded throughout the day. In some examples, the video segments also include metadata, which may include, for example, an indication of the detected emotional/cognitive state that triggered the recording, ongoing or periodic emotional/cognitive state indicators during the video segment, and/or an overlay that includes a dot, highlight, or other visual indicator of where the user was looking while the video was being recorded. In an example, any one or more components of the available metadata may be selectively visible while viewing a recorded video segment.

Figure 2:
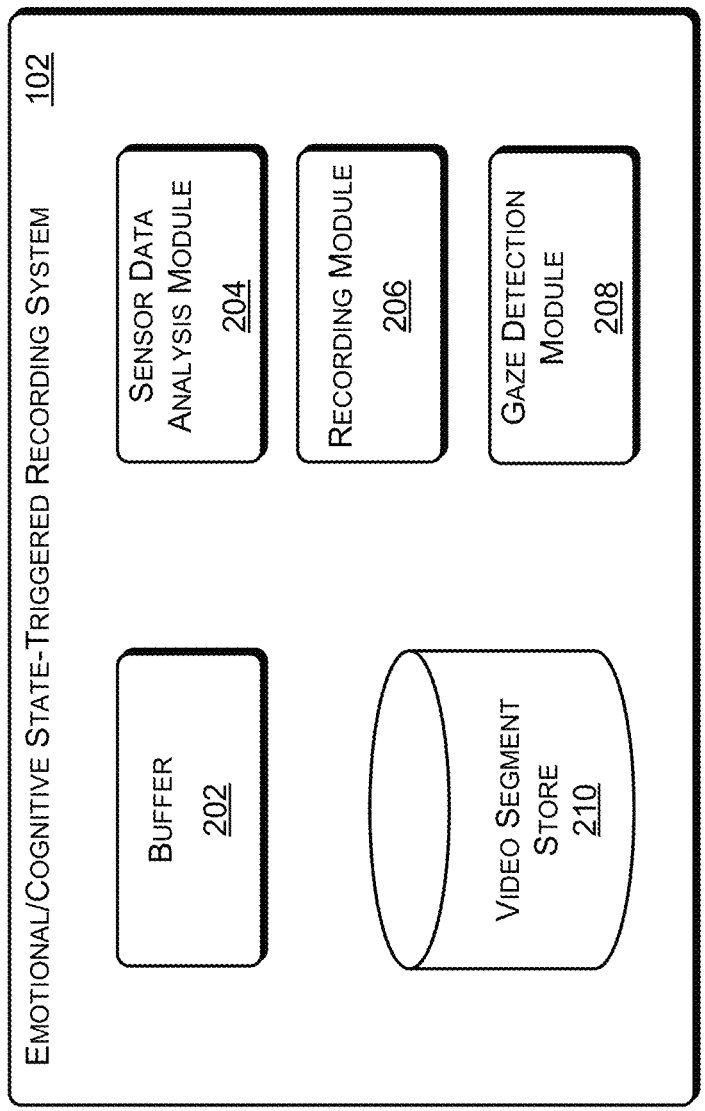
FIG. 2 is a block diagram illustrating example components of an emotional/cognitive state-triggered recording system.

FIG. 2 illustrates select components of emotional/cognitive state-triggered recording system 102, which may be implemented on a single device or may be distributed across multiple devices, such as HMD device 112, cell phone 116, and computing device 118. Example emotional/cognitive state-triggered recording system 102 includes buffer 202, sensor data analysis module 204, recording module 206, gaze detection module 208, and video segment store 210.

Buffer 202 is configured to store video and audio data as the video and audio data is received from camera 106 and microphone 108. In an example, buffer 202 is implemented as a five minute ring buffer.

Sensor data analysis module 204 receives sensor data from sensing device 104, and analyzes the received sensor data to determine an emotional or cognitive state of the user. In an example implementation, the received sensor data indicates an emotional or cognitive state. In an alternative implementation, the sensor data is analyzed using, for example, a deep neural network (DNN) to determine the emotional or cognitive state of the user. Sensor data analysis module 204 makes available data indicating the emotional or cognitive state of the user.

Recording module 206 determines, based on the data indicating the emotional or cognitive state of the user, whether or not to record a video segment. In an example, recording module 206 may be configured to initiate recording a video segment based on a change in the user's emotional or cognitive state. For example, recording module 206 may be configured to initiate recording a video segment when a user's emotional or cognitive state changes from a neutral state to a non-neutral state. In another example, recording module 206 may be configured to initiate recording a video segment when a value representing the user's emotional or cognitive state exceeds a threshold.

Recording module 206 also determines when to cease recording a particular video segment. For example, recording module 206 may record a video segment based on a predefined period of time, a change in emotional or cognitive state of the user, or a combination of the two. For example, when recording module 206 initiates recording a video segment, recording module 206 may cause the recording to continue for a predefined period of time (e.g., 10 minutes). Alternatively, recording module 206 may cause the recording to continue until sensor data indicates that the user's emotional or cognitive state has changed or has dropped below a threshold value. In another example, a predefined period of time may indicate a minimum or maximum length of a video segment to be recorded. In this example, if the predefined period of time indicates a minimum recording time, recording module 206 may cause the video segment to be recorded until the predefined period of time is met or until the user's emotional or cognitive state changes, whichever occurs later. If the predefined period of time indicates a maximum recording time, recording module 206 may cause the video segment to be recorded until the predefined period of time is met or until the user's emotional or cognitive state changes, whichever occurs first.

Gaze detection module 208 tracks the gaze of the user to determine a direction in which the user is looking. Gaze detection module 208 can be configured to generate, for example, a video overlay that includes a colored dot, highlight, or other visual indicator as to the direction of the user's gaze as the video was being captured.

Video segment store 210 is configured to store video segments that are recorded based on a user's emotional or cognitive state. For example, when recording module 206 initiates a recording, video and audio data stored in the buffer 202 is copied to a new video segment, which is stored in video segment store 210. Furthermore, recording module 206 directs additional video and audio data to be recorded to the video segment as described above. In an example implementation, video segment store 210 also stores metadata associated with a video segment, which may include, but is not limited to, an indicator of the user's emotional or cognitive state that triggered the recording, one or more indicators of the user's emotional or cognitive state as the video segment was being recorded, and an overlay to provide a visual indicator (e.g., a dot or highlight) of the position of the user's gaze as the video segment was being recorded.

Figure 3:
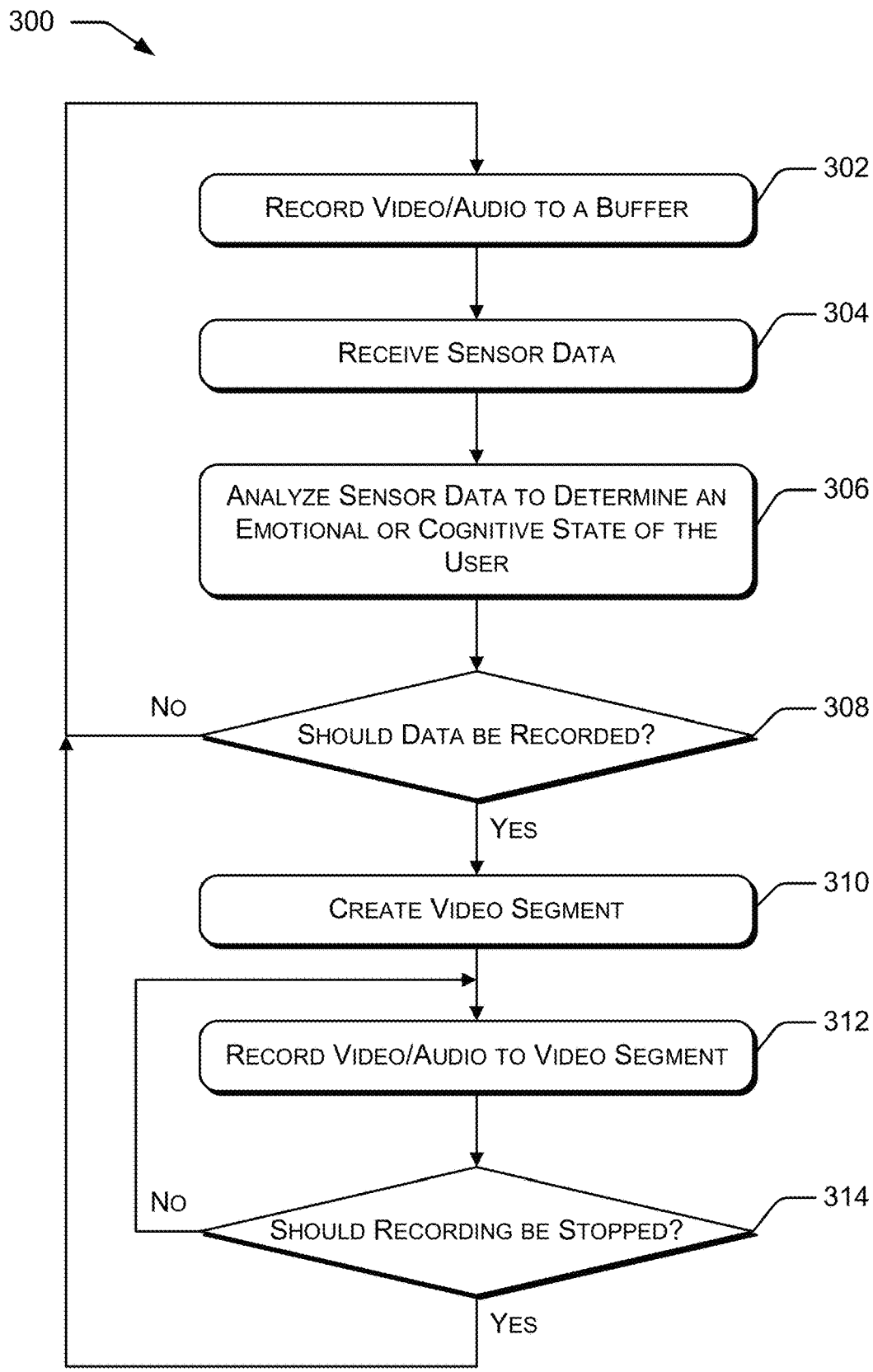
FIG. 3 is a flow diagram of an example method for performing emotional/cognitive state-triggered recording.

FIG. 3 illustrates an example method for performing emotional/cognitive state-triggered recording. The example process is illustrated as a collection of blocks in a logical flow graph, which represents a sequence of operations that can be implemented in hardware, software, or a combination thereof. The blocks are referenced by numbers. In the context of software, the blocks represent computer-executable instructions stored on one or more computer-readable media that, when executed by one or more processing units (such as hardware microprocessors), perform the recited operations. Generally, computer-executable instructions include routines, programs, objects, components, data structures, and the like that perform particular functions or implement particular abstract data types. The order in which the operations are described is not intended to be construed as a limitation, and any number of the described blocks can be combined in any order and/or in parallel to implement the process.

FIG. 3 illustrates an example method 300 for performing emotional/cognitive state-triggered recording. At block 302, video/audio is recorded to a buffer. For example, as video/audio data is captured by camera 106 and microphone 108, emotional/cognitive state-triggered recording system 102 writes the video/audio data to buffer 202. As described above, buffer 202 may be implemented as a ring buffer such that the buffer 202 continuously stores data from a most recent time period.

At block 304, sensor data is received. For example, sensor data analysis module 204 receives data from one or more sensing devices 104. As described above, the sensor data may include, but is not limited to, data indicating a galvanic skin response, data indicating a skin temperature, data indicating electrical activity of the brain, data indicating electrical activity of the heart, data indicating eye movements, data indicating facial expressions, data indicating pupil dilation and/or contraction, data indicating a volume of speech, or data indicating a rate of speech.

At block 306, the received sensor data is analyzed to determine an emotional or cognitive state of the user. For example, sensor data analysis module determines an emotional or cognitive state of the user based on the received sensor data. For example, the sensor data analysis module may utilize a deep neural network to analyze the received sensor data to determine the emotional or cognitive state of the user.

At block 308, it is determined whether or not data should be recorded. For example, based on the determined emotional or cognitive state of the user, recording module 206 determines whether or not to begin recording a video segment. For example, as described above, recording module 206 may determine to initiate recording a video segment based on a change in an emotional or cognitive state of the user, or based on a determination that a value representing an emotional or cognitive state of the user exceeds a threshold value.

If it is determined that data should not be recorded (the "No" branch from block 308), then processing continues as described above with reference to block 302.

On the other hand, if it is determined that data should be recorded (the "Yes" branch from block 308), then at block 310, a video segment is created. For example, recording module 206 creates a video segment by saving the contents of the buffer 202 to the video segment store 210. Additional data may also be stored in association with the video segment, such as, for example, an indicator of the current emotional or cognitive state of the user and/or an indicator of the current location of the user's gaze. In an example implementation, the direction of a user's gaze may be determined by gaze detection module 208.

At block 312, video/audio is recorded to the video segment. For example, in addition to, or instead of, recording the video/audio to the buffer, the recording module 206 causes additional captured video/audio to be recorded to the video segment that was created as described above with reference to block 310.

At block 314, it is determined whether or not the recording should be stopped. For example, as described above, recording module 206 may determine that the recording should be stopped after a pre-defined period of time and/or based on a change in the emotional/cognitive state of the user. For example, while recording the video, sensor data analysis module 204 may continue to analyze received sensor data, which may identify a change in (e.g., a return to a neutral) emotional/cognitive state of the user.

If it is determined that the recording should be stopped (the "Yes" branch from block 314), then recording to the video segment ceases, and processing continues as described above with reference to block 302.

On the other hand, if it is determined that the recording should not be stopped (the "No" branch from block 314), then processing continues as described above with reference to block 312, with the video/audio data continuing to be recorded to the video segment.

Emotional/Cognitive State Presentation

Figure 4:
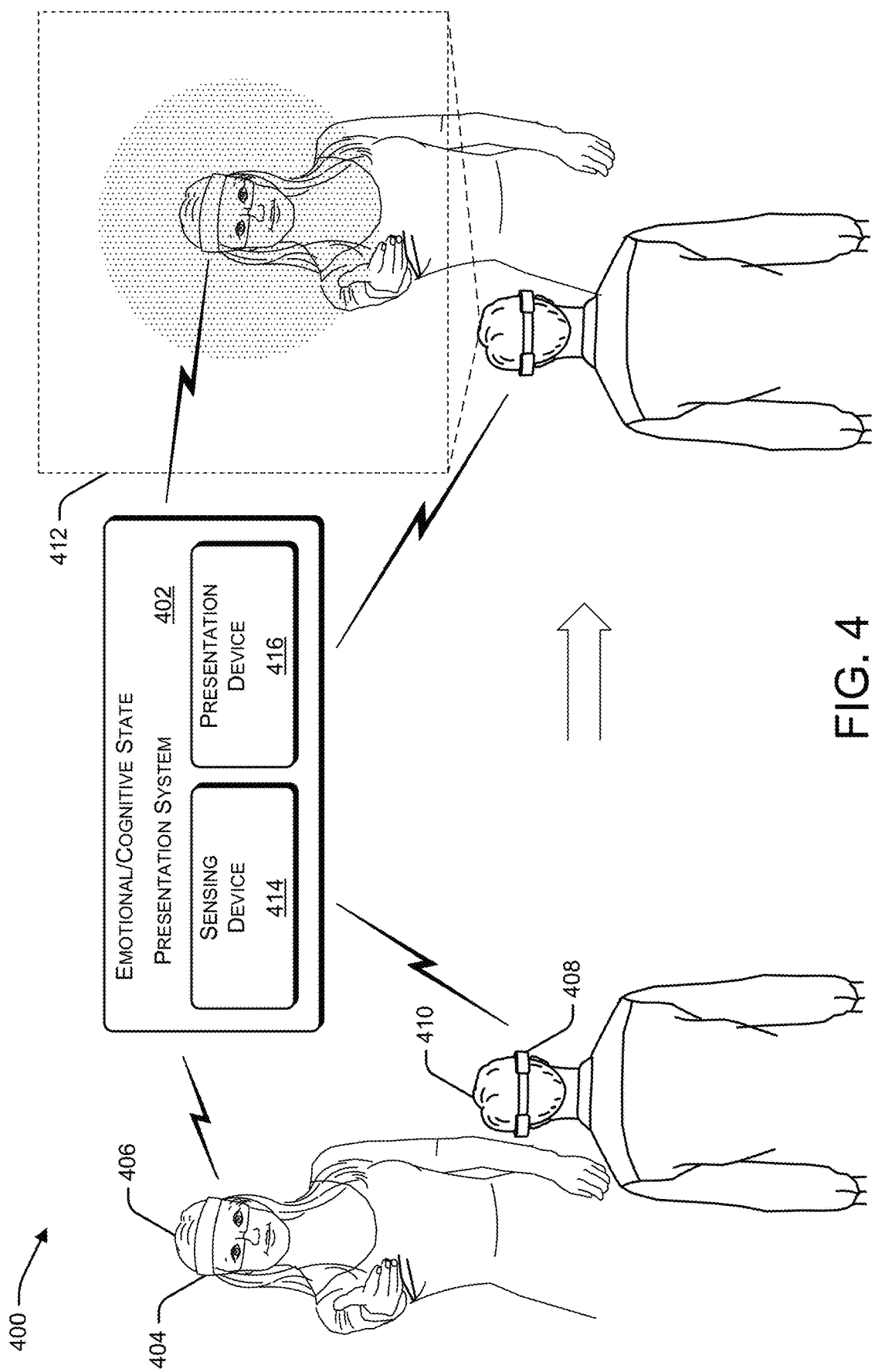
FIG. 4 is a pictorial diagram illustrating an example environment in which an emotional/cognitive state presentation system can be implemented.

FIG. 4 illustrates an example environment 400 in which emotional/cognitive state presentation can be implemented. Example environment 400 includes emotional/cognitive state presentation system 402, which enables emotional/cognitive state data to be shared between devices associated with two or more users. In the illustrated example, a first sensing/presentation device 404 is associated with a first user 406, and a second sensing/presentation device 408 is associated with a second user 410.

In an example implementation, user 406 selects, via device 404, to share data indicating her emotional/cognitive state. Similarly, user 410 selects, via device 408, to share data indicating his emotional/cognitive state. Sensors associated with device 404 indicate an emotional/cognitive state of user 406, while sensors associated with device 408 indicate an emotional/cognitive state of user 408. Device 404 and device 408 may communicate with one another directly, for example, via a Bluetooth connection, or via emotional/cognitive state presentation system 402 over a network.

When it is determined that device 404 and device 408 are within proximity to one another, data indicating the emotional/cognitive state of user 406 is shared with device 408 and data indicating the emotional/cognitive state of user 410 is shared with device 404. Upon receiving the data indicating the other user's emotional/cognitive state, sensing/presentation device 408 presents an indication of the emotion/cognitive state of user 406. In an example implementation, sensing/presentation device 408 provides an augmented reality view 412 that includes a visual aura 414 around user 406. For example, different colored auras can be used to indicate different emotions or cognitive states. Any number of other techniques may be used indicate the emotional or cognitive state of another user, including, but not limited to, an audio indicator, a text indicator, or a visual indicator.

Example emotional/cognitive state presentation system 402 includes a sensing device 414 and a presentation device 416. In the illustrated, non-limiting, example, device 404 and device 408 are implemented as a single device that includes a sensing device 414 and a presentation device 416.

Similar to the description above with reference to FIG. 1, sensing device 414 may be implemented as one or more devices, one or more of which may be worn or carried by the user. For example, sensors may be components of a HMD device, such as device 404 or device 408, or may be implemented as components of a cell phone, or any number of other devices.

In at least one example, the sensing device 414 can be any device or combination of devices configured to physiologically monitor a user. Individual sensors of one or more sensing devices 414 can include, but are not limited to, a galvanic skin response sensor for measuring galvanic skin response, a skin temperature sensor for measuring the temperature on the surface of the skin, an electroencephalography (EEG) device for measuring electrical activity of the brain, an electrocardiography (ECG or EKG) device for measuring electrical activity of the heart, cameras for tracking eye movement, facial expressions, pupil dilation and/or contraction, etc., sound sensors for measuring a volume of speech, a rate of speech, etc. In an example implementation, the sensor data can include measurements associated with a physiological attribute of a user, which can be an indicator of an emotional or cognitive state.

Presentation device 416 is configured to present to a user, an indication of an emotional or cognitive state of another user. In the example illustrated in FIG. 4, HMD device 408 includes a display for presenting an augmented reality, which may include a visual indicator of another user's emotional or cognitive state. In an alternate implementation, the presentation device 416 may be implemented as a component of any other device, such as a smart phone.

Figure 5:
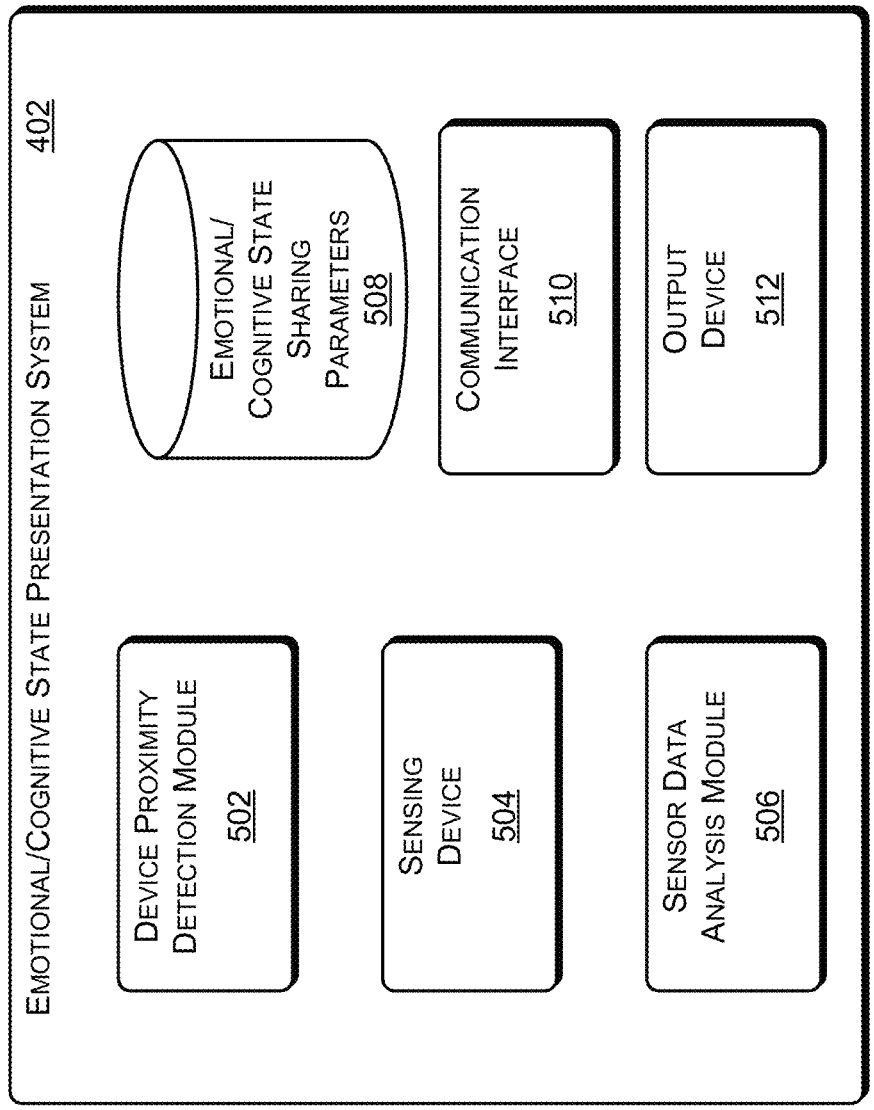
FIG. 5 is a block diagram illustrating example components of an emotional/cognitive state presentation system.

FIG. 5 illustrates select components of an example emotional/cognitive state presentation system. As illustrated in FIG. 5, example emotional/cognitive state presentation system 402 includes a device proximity detection module 502, sensing device 504, a sensor data analysis module 506, emotional/cognitive state sharing parameters 508, communication interface 510, and output device 512.

Device proximity detection module 502 is configured to detect another device that is in proximity. For example, referring to FIG. 4, a device proximity module may determine when device 404 and device 408 are within a pre-defined proximity to one another. In various examples, proximity may be determined based on global positioning system (GPS) data, Bluetooth availability, user input, and so on.

Sensing device 504 can be any device or combination of devices configured to physiologically monitor a user. Individual sensors of one or more sensing devices 504 can include, but are not limited to, a galvanic skin response sensor for measuring galvanic skin response, a skin temperature sensor for measuring the temperature on the surface of the skin, an electroencephalography (EEG) device for measuring electrical activity of the brain, an electrocardiography (ECG or EKG) device for measuring electrical activity of the heart, cameras for tracking eye movement, facial expressions, pupil dilation and/or contraction, etc., sound sensors for measuring a volume of speech, a rate of speech, etc. In an example implementation, the sensor data can include measurements associated with a physiological attribute of a user 406 or 410, which can be an indicator of an emotional or cognitive state.

Sensor data analysis module 506 receives sensor data from sensing device 504, and analyzes the received sensor data to determine an emotional or cognitive state of the user. In an example implementation, the received sensor data indicates an emotional or cognitive state. In an alternative implementation, the sensor data is analyzed using, for example, a deep neural network (DNN) to determine the emotional or cognitive state of the user. Sensor data analysis module 506 makes available data indicating the emotional or cognitive state of the user.

Emotional/cognitive state sharing parameters 508 may define, for example, a user's level of trust with other users for sharing emotional/cognitive state data. Emotional/cognitive state sharing parameters 508 may include default and/or user-specified parameters associated with emotional/cognitive state sharing. For example, a user may select specific emotions and/or cognitive states that are shareable, while designating others as private (non-shareable). As another example, a user may select specific user with whom they are willing to share emotional/cognitive state data and/or specific users with who they are not willing to share emotional/cognitive state data.

Communication interface 510 is configured to facilitate the sharing of emotional/cognitive state data between two user devices that are within proximity to one another. Communication interface 510 may include logic to verify a level of trust between the devices (e.g., based on the emotional/cognitive state sharing parameters 508 or input from a user), and to facilitate the transfer of data between the devices using a Bluetooth protocol or other network interface.

Output device 512 is configured to present data indicating an emotional or cognitive state of another user. For example, output device 512 may include, but is not limited to, a display device configured to allow for a real-world view of objects through the hardware display surface while also providing a rendered display of computer generated content or scenes (e.g., an aura surrounding an individual).

Figure 6:
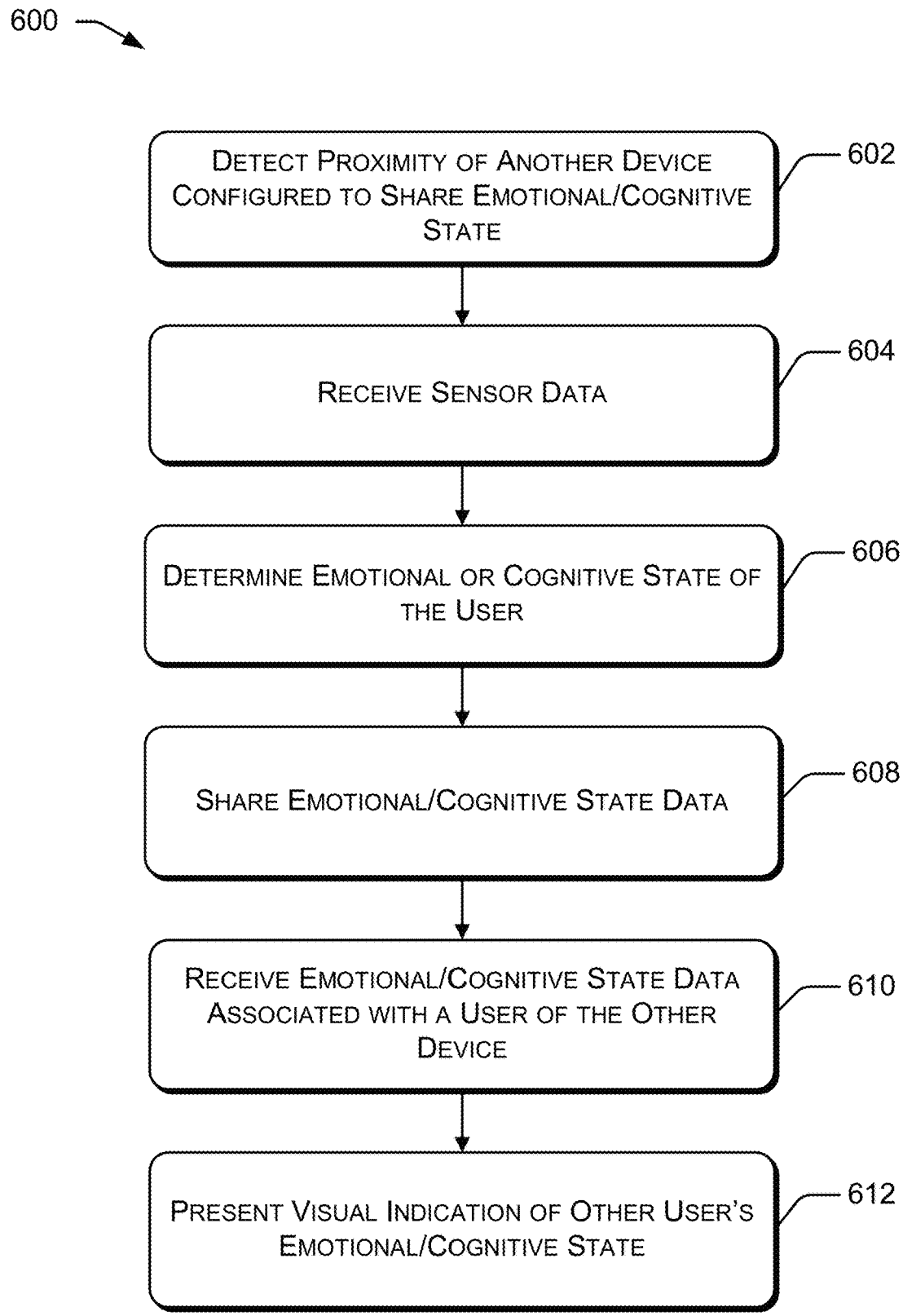
FIG. 6 is a flow diagram of an example method for performing emotional/cognitive state presentation.

FIG. 6 illustrates an example method for performing emotional/cognitive state presentation. The example process is illustrated as a collection of blocks in a logical flow graph, which represents a sequence of operations that can be implemented in hardware, software, or a combination thereof. The blocks are referenced by numbers. In the context of software, the blocks represent computer-executable instructions stored on one or more computer-readable media that, when executed by one or more processing units (such as hardware microprocessors), perform the recited operations. Generally, computer-executable instructions include routines, programs, objects, components, data structures, and the like that perform particular functions or implement particular abstract data types. The order in which the operations are described is not intended to be construed as a limitation, and any number of the described blocks can be combined in any order and/or in parallel to implement the process.

FIG. 6 illustrates an example method 600 for performing emotional/cognitive state presentation. At block 602, proximity of another device configured to share emotional/cognitive state is detected. For example, device proximity detection module 502 detects proximity of another device.

At block 604, sensor data is received. For example, sensor data analysis module 506 receives data from one or more sensing devices 504. As described above, the sensor data may include, but is not limited to, data indicating a galvanic skin response, data indicating a skin temperature, data indicating electrical activity of the brain, data indicating electrical activity of the heart, data indicating eye movements, data indicating facial expressions, data indicating pupil dilation and/or contraction, data indicating a volume of speech, or data indicating a rate of speech.

At block 606, an emotional or cognitive state of the user is determined. For example, sensor data analysis module 506 determines an emotional or cognitive state of the user based on the received sensor data. For example, the sensor data analysis module 506 may utilize a deep neural network to analyze the received sensor data to determine the emotional or cognitive state of the user.

At block 608, data indicating the determined emotional/cognitive state is shared. For example, an indication of a current emotional or cognitive state of the user is sent to the other device via communication interface 510. In an example implementation, communication interface 510 verifies a trusted relationship between the user and a user of the other device prior to sending the indication of the current emotional or cognitive state of the user. The trusted relationship may be verified based, for example, on emotional/cognitive state sharing parameters 508.

At block 610, data indicating an emotional/cognitive state of another user is received. For example, data indicating the emotional/cognitive state of the other user is received via the communication interface 510.

At block 612, the emotional/cognitive state of the other user is presented. For example, output device 512 may provide a real-world view of objects through the hardware display surface while also providing a rendered display of computer generated content or scenes (e.g., an aura surrounding an individual).

Example Architectures

Figure 7:
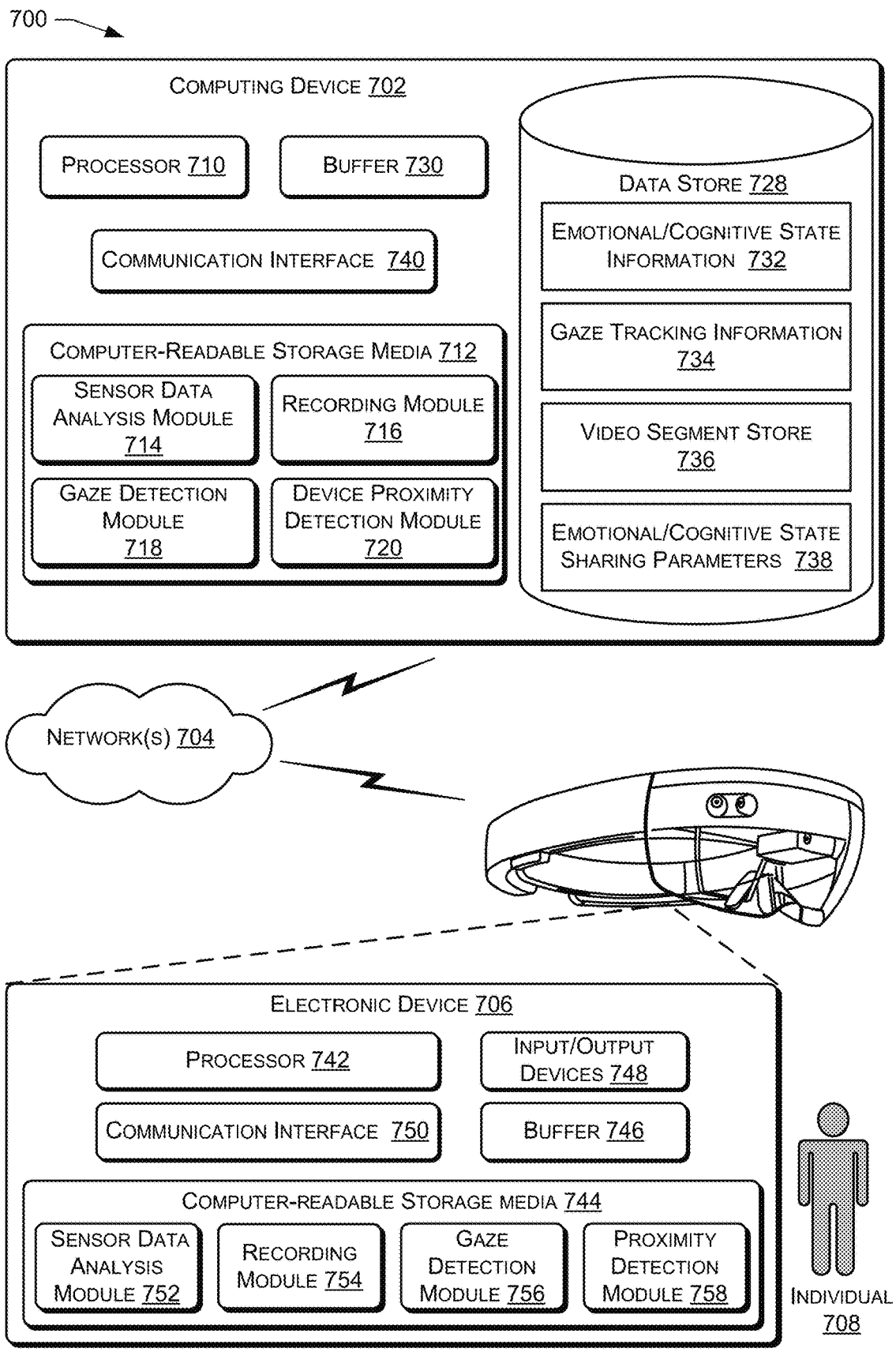
FIG. 7 is a block diagram illustrating an example system to identify objects using gaze tracking techniques.

FIG. 7 is a block diagram illustrating an example system 700 to record video based on emotional or cognitive states or to present emotional or cognitive states. The system 700 includes a computing device 702 that may be used to perform at least a portion of the operations to determine an emotional or cognitive state of a user and present the determined emotional or cognitive state or record video based on the determined emotional or cognitive state. The computing device 702 may be associated with an entity that is a service provider that provides services related to emotional/cognitive state presentation or video recording. Additionally, the computing device 702 may be associated with a manufacturer of the electronic device 706, a distributor of the electronic device 706, or both. The computing device 702 may include one or network interfaces (not shown) to communicate with other computing devices via one or more networks 704. The one or more networks 704 may include one or more of the Internet, a cable network, a satellite network, a wide area wireless communication network, a wired local area network, a wireless local area network, or a public switched telephone network (PSTN).

In particular embodiments, the computing device 702 may communicate via the one or more networks 704 with an electronic device 706 associated with an individual 708. The electronic device 706 may include a laptop computing device, a tablet computing device, a mobile communications device (e.g., a mobile phone), a wearable computing device (e.g., watch, glasses, fitness tracking device, a head mounted display, jewelry), a portable gaming device, combinations thereof, and the like. The individual 708 may utilize the electronic device 706 to record video or share/present data based on detected emotional/cognitive states of the individual 708.

The computing device 702 may include one or more processors, such as processor 710. The one or more processors 710 may include at least one hardware processor, such as a microprocessor. In some cases, the one or more processors 710 may include a central processing unit (CPU), a graphics processing unit (GPU), or both a CPU and GPU, or other processing units. Additionally, the one or more processors 710 may include a local memory that may store program modules, program data, and/or one or more operating systems.

In addition, the computing device 702 may include one or more computer-readable storage media, such as computer-readable storage media 712. The computer-readable storage media 712 may include volatile and nonvolatile memory and/or removable and non-removable media implemented in any type of technology for storage of information, such as computer-readable instructions, data structures, program modules, or other data. Such computer-readable storage media 712 may include, but is not limited to, RAM, ROM, EEPROM, flash memory or other memory technology, CD-ROM, digital versatile disks (DVD) or other optical storage, magnetic cassettes, magnetic tape, solid state storage, magnetic disk storage, RAID storage systems, storage arrays, network attached storage, storage area networks, cloud storage, removable storage media, or any other medium that may be used to store the desired information and that may be accessed by a computing device. Depending on the configuration of the computing device 702, the computer-readable storage media 712 may be a type of tangible computer-readable storage media and may be a non-transitory storage media.

The computer-readable storage media 712 may be used to store any number of functional components that are executable by the one or more processors 710. In many implementations, these functional components comprise instructions or programs that are executable by the one or more processors 710 and that, when executed, implement operational logic for performing the operations attributed to the computing device 702. Functional components of the computing device 702 that may be executed on the one or more processors 710 for implementing the various functions and features related to recording audio/video data based on detected emotional/cognitive states, as described herein, include a sensor data analysis module 714, a recording module 716, and a gaze detection module 718, which may correspond to, for example, sensor data analysis module 204, recording module 206, and gaze detection module 208, respectively, as shown in FIG. 2. One or more of the modules 714, 716, and 718 may be used to implement the emotional/cognitive state-triggered recording system 102 of FIG. 1 and FIG. 2.

Functional components of the computing device 702 that may be executed on the one or more processors 710 for implementing the various functions and features related to presenting emotional/cognitive states, as described herein, include the sensor data analysis module 714 and a device proximity detection module 720, which may correspond to, for example, sensor data analysis module 504 and device proximity detection module 502, respectively, as shown in FIG. 5. One or more of the modules 714 and 720 may be used to implement the emotional/cognitive state presentation system 402 of FIG. 4 and FIG. 5.

In various implementations, one or more of the functional components of components of the computing device 702 may be implemented as part of an integrated circuit that is part of, or accessible to, computing device 702. For example, the sensor data analysis module may be implemented, at least in part, as using an application specific integrated circuit (ASIC) specialized for the execution of a deep neural network (DNN).

The computing device 702 may also include, or is coupled to, a data store 728 and a buffer 730, which may include, but are not limited to, RAM, ROM, EEPROM, flash memory, one or more hard disks, solid state drives, optical memory (e.g. CD, DVD), or other non-transient memory technologies. The data store 728 may maintain information that is utilized by the computing device 702 to perform operations related to emotional/cognitive state-triggered recording or emotional/cognitive state presentation. For example, the data store 728 may include emotional/cognitive state information 732, gaze tracking information 734 related to determining gaze of an individual, a video segment store 736, and/or emotional/cognitive state sharing parameters 738.

Emotional/cognitive state information 732 may include, for example, a sensor values corresponding to various emotional and cognitive states.

The gaze tracking information 734 stored in the data store 728 may include information used to determine gaze of an individual. In some cases, the gaze tracking information 734 may include eye position data for one or more individuals. In addition, the gaze tracking information 734 may include distances of facial features of individuals, reference points, and other information that may be used to determine gaze of an individual. Optionally, portions of the gaze tracking information 734 may be cached or otherwise stored temporarily as gaze calculations are performed. After gaze calculations are performed, at least a portion of the gaze tracking information 734 may be discarded to minimize the memory resources used to identify objects using gaze tracking techniques.

Video segment store 736 may be configured to store video/audio segments and related metadata recorded based on detected emotional or cognitive states of a user. For example, video segment store 736 may correspond to video segment store 210 shown in FIG. 2.

Emotional/cognitive state sharing parameters 738 may include default and/or user-specified parameters associated with emotional/cognitive state sharing. For example, a user may select specific emotions and/or cognitive states that are shareable, while designating others as private (non-shareable). As another example, a user may select specific user with whom they are willing to share emotional/cognitive state data and/or specific users with who they are not willing to share emotional/cognitive state data.

Buffer 730 is configured to store video/audio data when emotional/cognitive state-triggered recording is active. For example, upon activation of the emotional/cognitive state-triggered recording system 102 by a user (e.g, through a user interface or via a hardware switch), video/audio data is continuously recorded to buffer 730 in anticipation of a detected change in emotional/cognitive state that will trigger recording to a video segment in video segment store 736.

The sensor data analysis module 714 may include computer-readable instructions that are executable by the processor 710 to receive sensor data and analyze the received sensor data to determine an emotional or cognitive state of the user. In an example implementation, the received sensor data indicates an emotional or cognitive state. In an alternative implementation, the sensor data is analyzed using, for example, a deep neural network (DNN) to determine the emotional or cognitive state of the user. Sensor data analysis module 714 makes available data indicating the emotional or cognitive state of the user.

The recording module 716 may include computer-readable instructions that are executable by the processor 710 to determine, based on the data indicating the emotional or cognitive state of the user, whether or not to record, and when to cease recording, a video segment.

The gaze detection module 718 may include computer-readable instructions that are executable by the processor 710 to obtain data that may be used to determine a gaze path of an individual. In some cases, the gaze detection module 718 may obtain data from the electronic device 706 that may be used to determine gaze of an individual, such as the individual 708. For example, the gaze detection module 718 may obtain data indicating the position of at least one eye of an individual. In various implementations, the gaze detection module 718 may obtain images of at least one eye of an individual and analyze the images to determine eye position of an individual. The eye positions of an individual may be used to determine the gaze path of the individual. In particular implementations, the eye positions of an individual may be used to determine a direction in which an individual is looking. In some cases, the gaze path of an individual may be approximated as a cone shaped field of view or a triangular prism shaped field of view into a scene.

The gaze detection module 718 may also generate a video overlay to be stored as metadata with a video segment in video segment store 736, where the video overlay includes a visible dot, highlight, or other visual indicator of the gaze path of the individual while the video segment was being recorded.

The device proximity detection module 720 may include computer-readable instructions that are executable by the processor 710 to detect another device that is in proximity.

The computing device 702 may also include a communication interface 740, which is configured to enable sharing of data with other devices, such as sharing of data indicating an emotional or cognitive state of a user.

The electronic device 706 of the system 700 may include a processor 742, computer-readable storage media 744, a buffer 746, input/output device 748, and a communication interface 750. The processor 742 may include a hardware-processing unit, such as a central processing unit, a graphics processing unit, a DNN chip, or any combination thereof. In an implementation, the computer-readable storage media 744 may include volatile and nonvolatile memory and/or removable and non-removable media implemented in any type of technology for storage of information, such as computer-readable instructions, data structures, program modules, or other data. Such computer-readable storage media 744 may include, but is not limited to, RAM, ROM, EEPROM, flash memory or other memory technology, CD-ROM, digital versatile disks (DVD) or other optical storage, solid state storage, magnetic disk storage, removable storage media, or any other medium that may be used to store the desired information and that can be accessed by the electronic device 706. Depending on the configuration of the electronic device 706, the computer-readable storage media 744 may be a type of tangible computer-readable storage media and may be a non-transitory storage media. The electronic device 706 may also include one or network interfaces (not shown) to communicate with other computing devices via the one or more networks 704.

Buffer 746 may be configured to record video/audio to support emotional/cognitive state-triggered video recording. As illustrates in FIG. 7, a buffer may be a component of computing device 702 and or electronic device 706.

The input/output devices 748 may include one or more sensors. In at least one example, the input/output devices 748 may include sensor(s) that may include any device or combination of devices configured to sense conditions of the individual 708 or surroundings of the individual 708. The input/output devices 748 may include the sensing device 104 shown in FIG. 1. The input/output devices 748 may include one or more user facing cameras or other sensors for tracking eye movement or gaze, facial expressions, pupil dilation and/or contraction, gestures, and/or other characteristics of the user. In some examples, the input/output devices 748 may include one or more outwardly facing or environmental cameras for capturing images of real-world objects and surroundings of the individual 708, such as, for example, camera 106 described above with reference to FIG. 1. The input/output devices 748 may additionally or alternatively include one or more biometric sensors (e.g., a galvanic skin response sensor for measuring galvanic skin response, a heart rate monitor, a skin temperature sensor for measuring the temperature on the surface of the skin, an electroencephalography (EEG) device for measuring electrical activity of the brain, an electrocardiography (ECG or EKG) device for measuring electrical activity of the heart), one or more other cameras (e.g., web cameras, infrared cameras, depth cameras, etc.), microphones (e.g., microphone 108) or other sound sensors for measuring a volume of speech, a rate of speech, etc., light sensors, optical scanners, or the like.

Individual input/output devices 748 may output data to one or more module(s) for suitable processing, such as a sensor data analysis module 752, a recording module 754, a gaze detection module 756, and a proximity detection module 758. For instance, a biometric sensor may capture sensor data which may be processed by the sensor data analysis module 752 to determine an emotional or cognitive state of the user. The sensor data analysis module 752 may then output an indicator of the emotional or cognitive state of the user to the recording module 754, which may then process audio and video data captured by a microphone and camera to generate a video segment to be stored in video segment store 736.

As another example, a user facing camera may capture gaze tracking data which may be processed by the gaze detection module 756 to determine a gaze path of the individual 708. The gaze detection module 756 may then output the gaze path to the recording module 754 or to the computing device 702 to generate metadata to be stored in association with a video segment in video segment store 736.

In additional and/or alternative examples, the input/output devices 748 may include any device or combination of devices configured to detect a position or movement of the electronic device 706 and other objects. For instance, the input/output devices 748 may additionally and/or alternatively include a depth map sensor, a light field sensor, a gyroscope, a sonar sensor, an infrared sensor, a compass, an accelerometer, a global positioning system (GPS) sensor, and/or any other device or component for detecting a position or movement of the electronic device 706 and/or other objects. The input/output devices 748 may also enable the generation of data characterizing interactions, such as user gestures, with the electronic device 706. For illustrative purposes, the input/output devices 748 may enable the generation of data defining a position and aspects of movement, e.g., speed, direction, acceleration, of one or more objects, which may include the electronic device 706, physical items near the electronic device 706, and/or users.

In some implementations, at least some of the input/output devices 748 may be part of, or built into, the electronic device 706. More specifically, the electronic device 706 may include a user facing camera sensor and/or an environmental camera disposed in or integrated with a nose-bridge component of the electronic device 706. As described above, the electronic device 706 may include any configuration of one or more input/output devices 748 that may be part of, or built into, the electronic device 706. However, in some examples, one or more of the input/output devices 748 may be removably coupled to the electronic device 706, or be separate from and communicatively coupled to the electronic device 706. In the latter case, data from the input/output devices 748 may be communicated from the input/output devices 748 to the electronic device 706, for example, via a wired and/or wireless network, such as network 704.

Additionally, input/output devices 748 may include one or more input interfaces that may include a keyboard, keypad, mouse, microphone, touch sensor, touch screen, joystick, control buttons, scrolling buttons, cameras, neural interface, or any other device suitable to generate a signal and/or data defining a user interaction with the electronic device 706. By way of example and not limitation, the input/output devices 748 may include a display (e.g., holographic display, head-up display, protector, touch screen, liquid crystal display (LCD), etc.), speakers, haptic interfaces, or the like.

In at least one example, a display device of the electronic device 706 may include a hardware display surface that may be configured to allow for a real-world view of objects through the hardware display surface while also providing a rendered display of computer generated content or scenes (e.g., an aura surrounding an individual). The hardware display surface may include one or more components, such as a projector, screen, or other suitable components for producing a display of an object and/or data. In some configurations, the hardware display surface may be configured to cover at least one eye of a user. In one illustrative example, the hardware display surface may include a screen configured to cover both eyes of a user. The hardware display surface may render or cause the display of one or more images for generating a view or a stereoscopic image of one or more computer generated virtual objects. For illustrative purposes, an object can be an item, data, device, person, place, or any type of entity. In at least one example, an object can be associated with a function or a feature associated with an application. Some configurations may enable the electronic device 706 to graphically associate holographic user interfaces and other graphical elements with an object seen through a hardware display surface or rendered objects displayed on the hardware display surface of the electronic device 706.

A hardware display surface of the electronic device 706 may be configured to allow the individual 708 to view objects from different environments. In some configurations, the hardware display surface may display a rendering of a computer generated virtual object. In addition, some configurations of the hardware display surface may allow the individual 708 to see through selectable sections of the hardware display surface having a controllable level of transparency, enabling the individual 708 to view objects in his or her surrounding environment. For illustrative purposes, a perspective of the individual 708 looking at objects through the hardware display surface may be referred to herein as a "real-world view" of an object or a "real-world view of a physical object." Computer generated renderings of objects and/or data may be displayed in, around, or near the selected portions of the hardware display surface enabling the individual 708 to view the computer generated renderings along with real-world views of objects observed through the selected portions of the hardware display surface.

Some configurations described herein provide both a "see through display" and an "augmented reality display." For illustrative purposes, the "see through display" may include a transparent lens that may have content displayed on it. The "augmented reality display" may include an opaque display that is configured to display content over a rendering of an image, which may be from any source, such as a video feed from a camera used to capture images of an environment. For illustrative purposes, some examples described herein describe a display of rendered content over a display of an image. In addition, some examples described herein describe techniques that display rendered content over a "see through display" enabling a user to see a real-world view of an object with the content. It can be appreciated that the examples of the techniques described herein can apply to a "see through display," an "augmented reality display," or variations and combinations thereof. For illustrative purposes, devices configured to enable a "see through display," "augmented reality display," or combinations thereof are referred to herein as devices that are capable of providing a "mixed environment" or "mixed reality scene."

In some implementations, at least a portion of the operations performed by the sensor data analysis module 752 may include operations performed by the sensor data analysis module 714, at least a portion of the operations performed by the recording module 754 may include operations performed by the recording module 716, at least a portion of the operations performed by the gaze detection module 756 may include operations performed by the gaze detection module 718, and at least a portion of the operations performed by the proximity detection module 758 may include operations performed by the device proximity detection module 720, or combinations thereof.

Communication interface 750 is configured to enable sharing of data with other devices, such as sharing of data indicating an emotional or cognitive state of a user. In some implementations, at least a portion of the operations performed by the communication interface 750 may include operations performed by the communication interface 740.

Figure 8A:
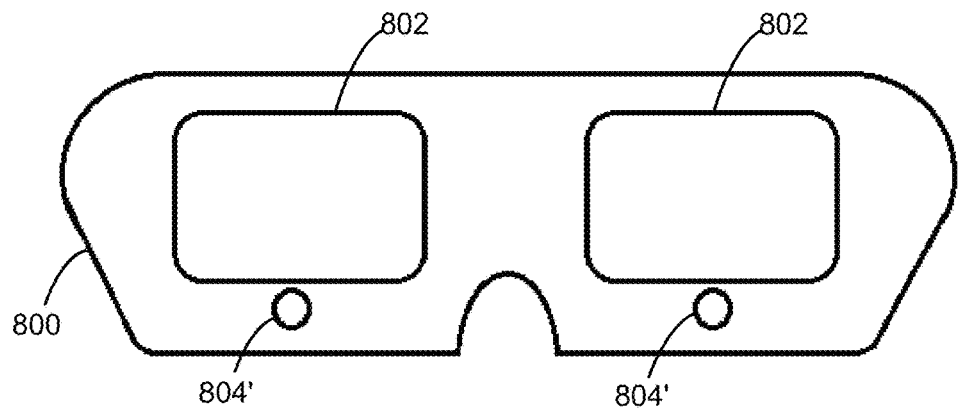
FIG. 8A-FIG. 8C illustrate example details of identifying gaze targets by tracking gaze of an individual.

Referring now to FIGS. 8A-8C, 9A-9F, 10A-10F, and 11 the following sections describe techniques for detecting a gaze path. The techniques are described in the context of a head-mounted computing device having a user facing gaze tracking camera. However, the techniques described in these sections may also be applied to other types of computing devices having a user facing camera for gaze tracking (e.g., computer with a web camera, a tablet or smartphone with user-facing camera, a game console with user facing camera, etc.). FIG. 8A is back view of a device 800 (e.g., HMD device 112, 404, 408, or 706) having one or more hardware display surfaces 802 and one or more sensors 804 and 804'. In at least one example, sensor(s) 804' are user facing and may be configured to track the position of at least one eye of a user. In addition, at least one other sensor 804 may be a scene-facing camera (e.g., camera 106) and may be directed toward a real-world object for generating image data of the real-world object. As will be described in more detail below, examples may process eye position data, image data, and other data to identify a gaze path of the user. As will also be described below, examples described herein may also determine if the user is looking at a particular section of a hardware display surface 802, a particular part of a real-world object, or a particular part of a rendered object. Such information may be useful for determining gaze targets from gaze tracking data, where the gaze targets can be identified in a recorded video segment.

In FIG. 8A, the device 800 comprises two of the user facing sensors 804' for generating data or a signal indicating the position or movement of at least one eye of a user. The sensors 804' may be in the form of a camera or another suitable device for tracking the position or movement of at least one eye of the user. The device 800 may also comprise at least one hardware display surface 802 for allowing a user to view one or more objects. The hardware display surface 802 may provide a view of a real-world object through the hardware display surface 802 as well as images of rendered objects that may be displayed on the hardware display surface 802, as described above.

Figure 8B:
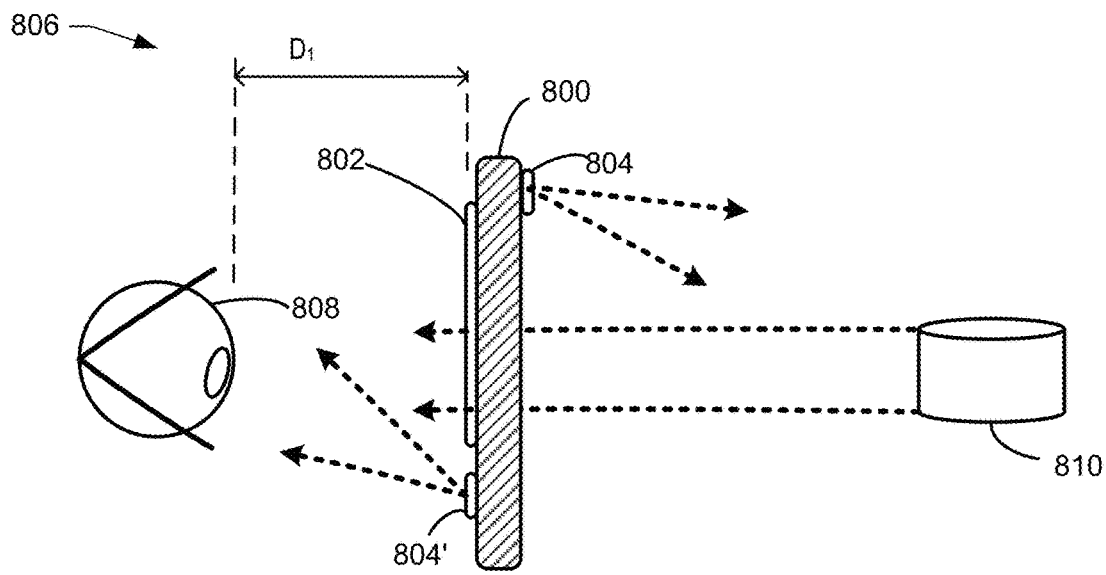

FIG. 8B is a side cutaway view 806 of the device 800 shown in FIG. 8A. FIG. 8B includes an eye 808 of a user looking through the hardware display surface 802. The hardware display surface 802 is configured to create transparent sections enabling a user to view objects through the hardware display surface 802. FIG. 8B shows an example arrangement where a real-world object 810 is aligned with a transparent section of the hardware display surface 802 allowing the user to view the real-world object 810 through the hardware display surface 802. The hardware display surface 802 may display one or more rendered objects. The device 800 also comprises at least one sensor 804' directed toward at least one eye 808 of the user.

Figure 8C:
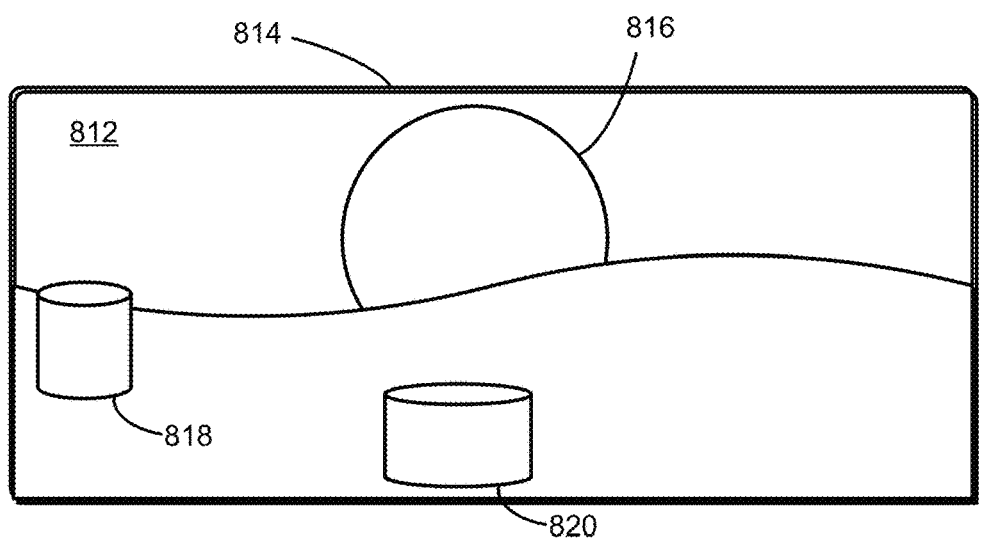

FIG. 8C illustrates an example scene or view 812 that may be observed by a user via the hardware display surface 802. The thick double line 814 illustrates the boundary of the hardware display surface 802. In this illustrative example, the scene or view 812 includes a real-world object 816, a first rendered object 818, and a second rendered object 820 that are displayed on the hardware display surface 802. The real-world object 816 is viewed through the hardware display surface 802.

The device 800 may utilize one or more techniques for calibrating the device 800. The following section, in conjunction with FIGS. 9A-9F, describes aspects of a technique for obtaining calibration data. A subsequent section, in conjunction with FIG. 10A-FIG. 10F, describes aspects of an example scenario where a device 800 processes the calibration data and other data to identify a gaze target.

A device 800 may be calibrated in a number of ways. In one example, a device 800 may utilize the display of a number of graphical elements at predetermined locations. As the graphical elements are displayed, the device 800 may prompt the user to look at a particular graphical element and provide an input to verify that the user is looking at the particular graphical element. When the user verifies that he or she is looking at the particular graphical element, sensor(s) 804' may generate eye position data defining a position of at least one eye. The eye position data may be stored in a data structure in memory in response to receiving the verification from the user.

Figure 9A:
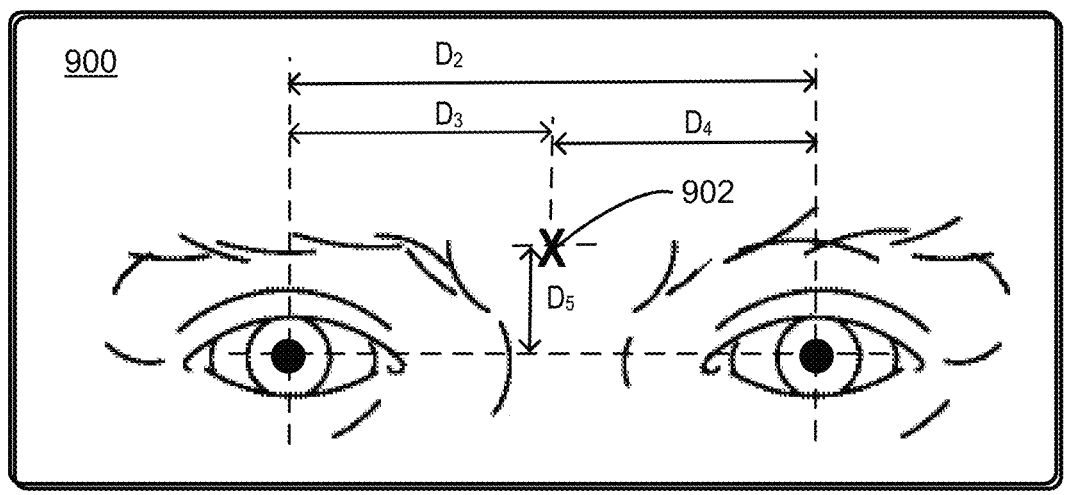
FIG. 9A-FIG. 9F describe example techniques for obtaining calibration data for gaze tracking.

FIG. 9A illustrates an example view 900 that may be captured by the sensors 804' of the device 800. From such a perspective, the device 800 may determine one or more values that define the position of at least one eye 808 of the user. In one illustrative example, the values may include a second value (D2) indicating a distance between a user's eyes and a third value (D3), fourth value (D4), and a fifth value (D7) indicating a distance between at least one eye of the user and a reference point 902. It may be appreciated that by the use of one or more image processing technologies, one or more aspects of an eye, such as the pupil, may be identified and utilized to determine an eye position.

In addition, by the use of one or more suitable technologies, a reference point 902 may be selected. A reference point 902 may be based on a feature of the user, e.g., a tip of a nose, an eyebrow, a beauty mark, or a reference point 902 may be in an arbitrary location. In the example of FIG. 9A, a point between the user's eyes is used as a reference point 902. This example reference point 902 is provided for illustrative purposes and is not to be construed as limiting. It may be appreciated that the reference point 902 may be in any suitable location, which may be based on an identifiable feature or characteristic of a user or any object.

Figure 9B:
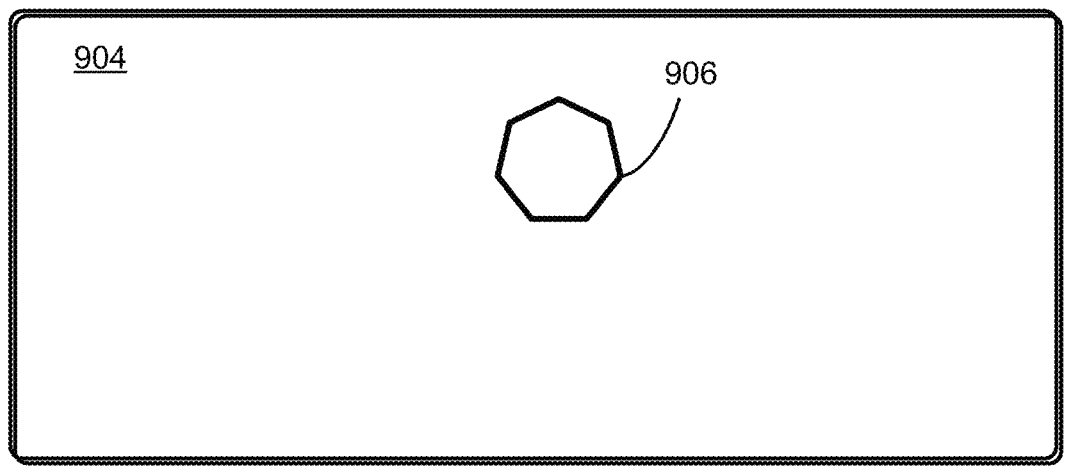

As described above, the device 800 may generate a number of graphical elements at predetermined locations of the hardware display surface 802. As the graphical elements are displayed on the hardware display surface 802, the device 800 may prompt the user to look at the graphical elements and provide an input to verify that the user is looking at the graphical elements. FIG. 9B illustrates an example view 904 of a graphical element 906 that may be generated by the device 800 to facilitate the calibration process. In this example, the device 800 generates a rendering of a graphical element 906 in the center of the viewing area. While the graphical element 906 is displayed, the device 800 may generate a prompt for the user to verify that he or she is looking at the graphical element 906. The prompt, as well as a user response to the prompt, may include a gesture, voice command, or other suitable types of input.

When the device 800 verifies that the user is looking at the graphical element 906, the device 800 may record one or more values indicating the position and/or the movement of at least one eye 808 of the user. For instance, one or more values described above and shown in FIG. 8B and FIG. 9A may be stored in a data structure in memory. It may be appreciated that any suitable value or a combination of values may be stored and utilized, including but not limited to, the first value (D1) indicating the distance between the sensors 804' and at least one eye 808 of a user, the second value (D2) indicating the distance between the eyes of a user, and other values (D3, D4, and D7) indicating the distance between at least one eye 808 and a reference point 902. These values are provided for illustrative purposes and are not to be construed as limiting. It may be appreciated that such values, subsets of such values, and other values of other measurements may be utilized in determining the movement and/or the position of one or more eyes of a user.

Figure 9C:
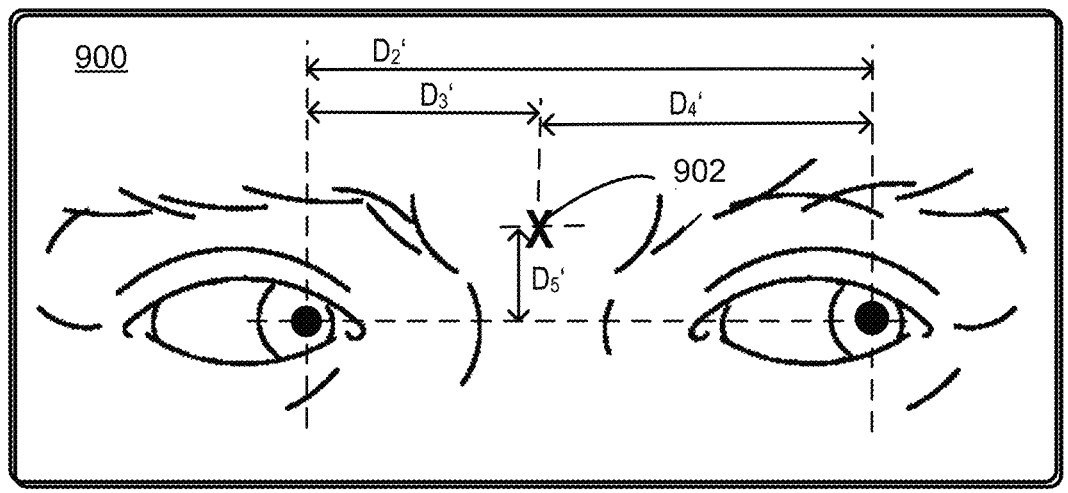
Figure 9D:
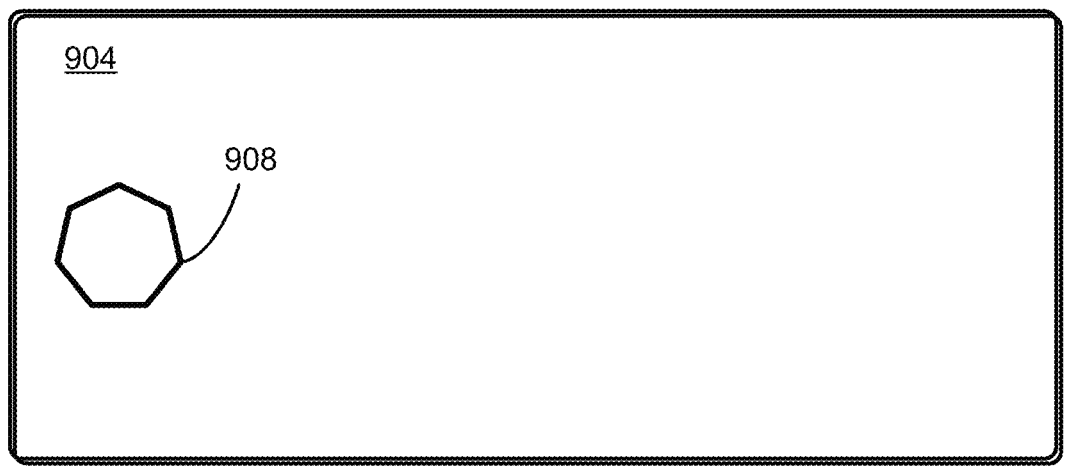
Figure 9E:
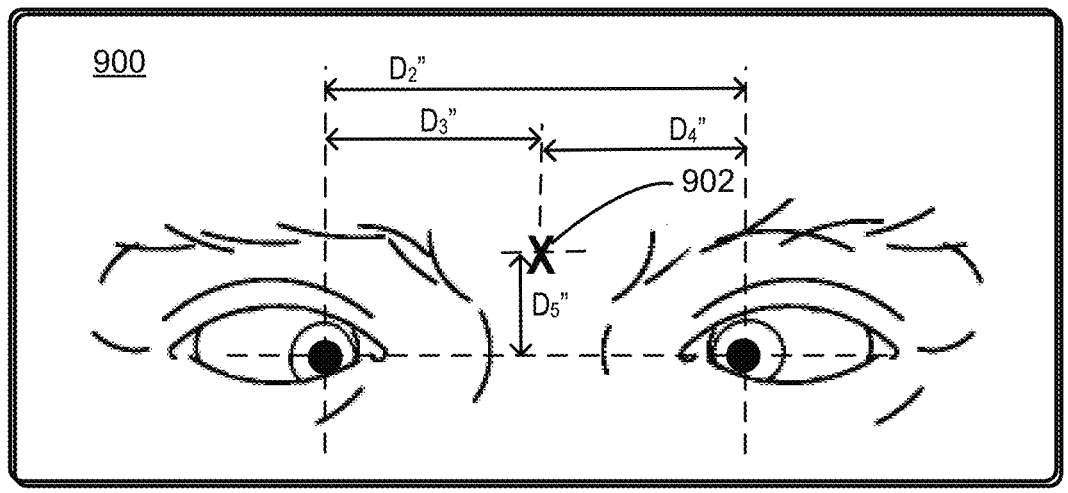
Figure 9F:
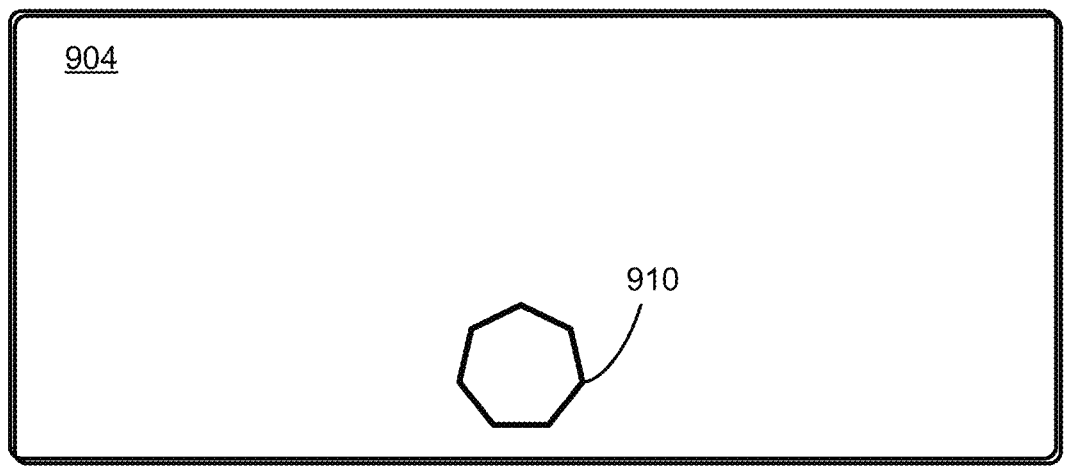

Other sets of values may be measured during the display of other graphical elements displayed in various positions. For example, as shown in FIG. 9C, a second set of values (D2', D3', D4', and D7') may be measured when a second graphical element 908 is displayed, as shown in FIG. 9D. As shown in FIG. 9E, a third set of values (D2", D3", D4", and D7") may be measured when a third graphical element 910 is displayed, as shown in FIG. 9F.

These example measurements and the locations of the graphical elements are provided for illustrative purposes. It may be appreciated that any number of graphical elements may be placed at different locations to obtain measurements that may be used to calibrate a device 800. For example, the device 800 may sequentially display a graphical element at pre-determined locations of the view 904, such as each corner of the view 904. As may be appreciated, more or fewer graphical elements may be used in the calibration process.

The values that indicate the position of at least one eye 808 at each pre-determined location may be used to generate calibration data. The calibration data may be configured to correlate the sets of eye position data with data identifying the positions of the graphical elements.

Any known technique suitable for generating calibration data may be used. It may be appreciated that the generation of calibration data may include extrapolation, projection and/or estimation technologies that may project correlations between sets of eye position data and various sections of a hardware display surface 802 and/or pixels of a hardware display surface 802. These examples are provided for illustrative purposes and are not to be construed as limiting, and the values and/or calibration data may be obtained in other ways, including receiving such calibration data from one or more remote resources.

Once the calibration data is generated or obtained, such data and other data may be utilized by the device 800 to determine if a user is looking at a particular gaze target, which may include a part of a hardware display surface 802, a rendered object, part of a rendered object, a real-world object, or part of a real-world object. FIGS. 10A-10F describe aspects of an example scenario where the device 800 having at least one sensor 804' is used to track the movement of at least one eye 808 of a user to identify a gaze target.

Figure 10A:
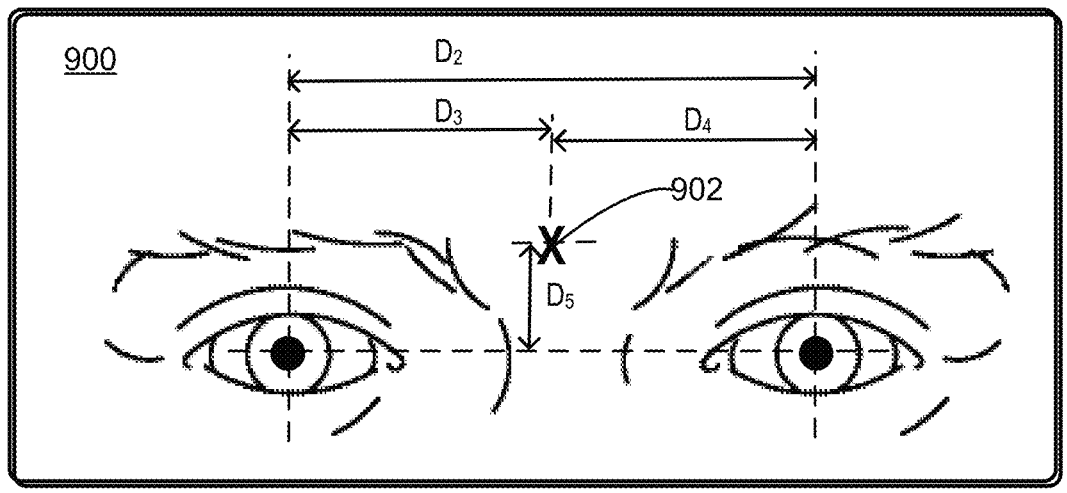
FIG. 10A-FIG. 10F describe example techniques for processing calibration data and other data to identify a gaze target.
Figure 10B:
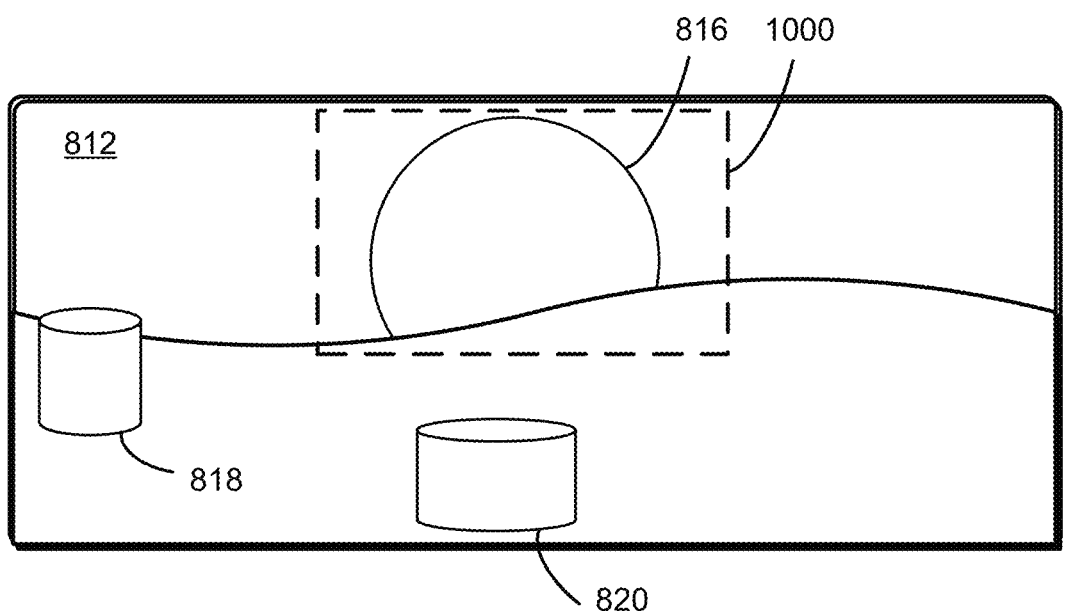

Referring now to FIG. 10A and FIG. 10B, an example scenario showing the identification of a gaze target is shown and described. In this example, the user is looking at the example view 812. As summarized above with reference to FIG. 8C, the example view 812 comprises both a view of rendered objects (e.g., first rendered object 818 and second rendered object 820) on the hardware display surface 802 as well as a view of a real-world object 816 through the hardware display surface 802. While the user is looking at the view 812, the sensor(s) 804' may cause the generation of one or more measured values, such as the values shown in the FIG. 10A. In some examples, using any combination of suitable technologies, such values may be compared against the calibration data and/or other data to identify a gaze target. In this example, one or more values measured in the scenario depicted in FIG. 10A may be processed with the calibration data to determine that the user is looking at the real world object 816. In such an example, the one or more measured values shown in FIG. 10A may also be used to determine that the user is looking at a predetermined section of an interface, such as the first section 1000 of the hardware display surface 802 in FIG. 10B.

Figure 10C:
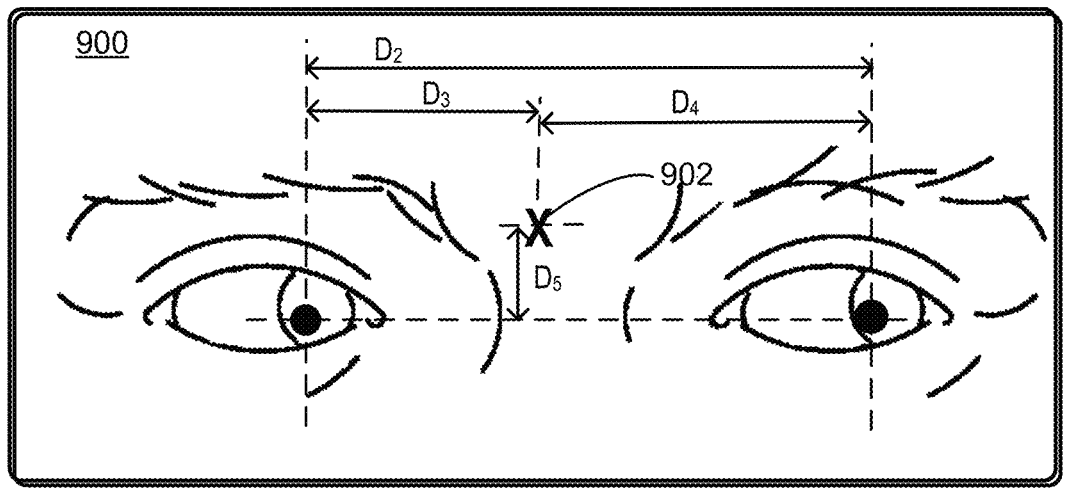
Figure 10D:
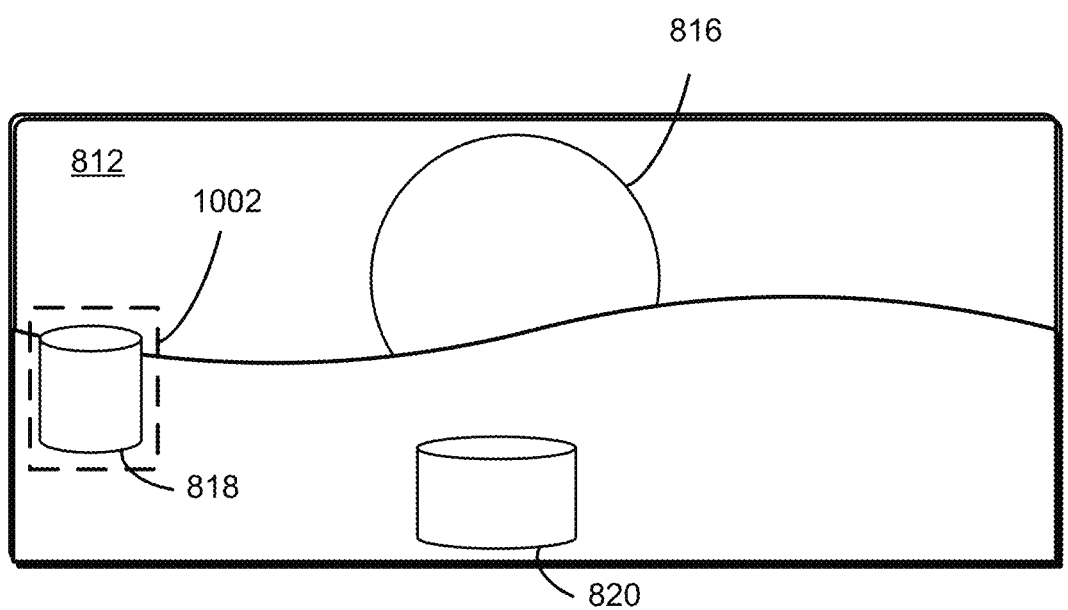

In continuing the present example, one or more values measured in the scenario depicted in FIG. 10C may be processed with the calibration data to determine that the user is looking at the second rendered object 818. In such an example, the one or more measured values shown in FIG. 10C may also be used to determine that the user is looking at a second section 1002 of the hardware display surface 802 in FIG. 10D.

Figure 10E:
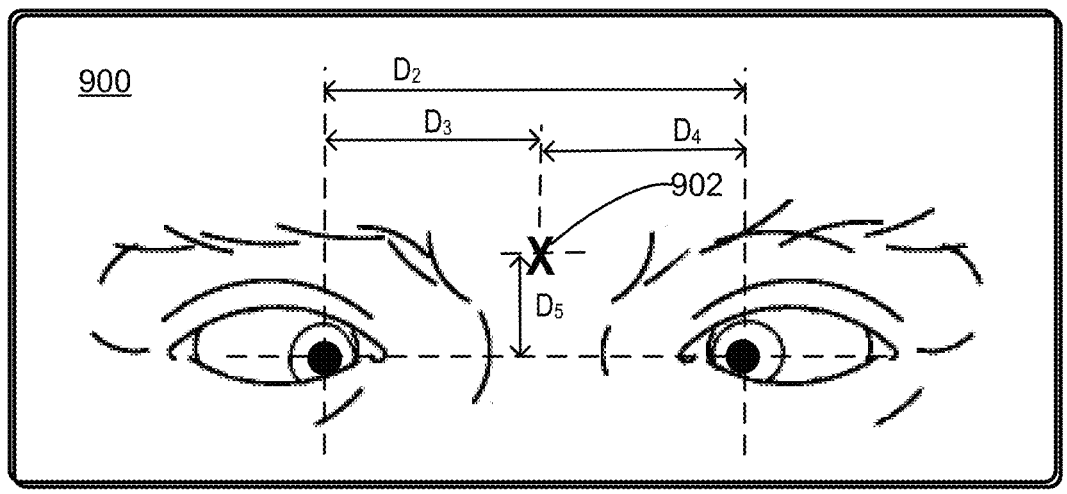
Figure 10F:
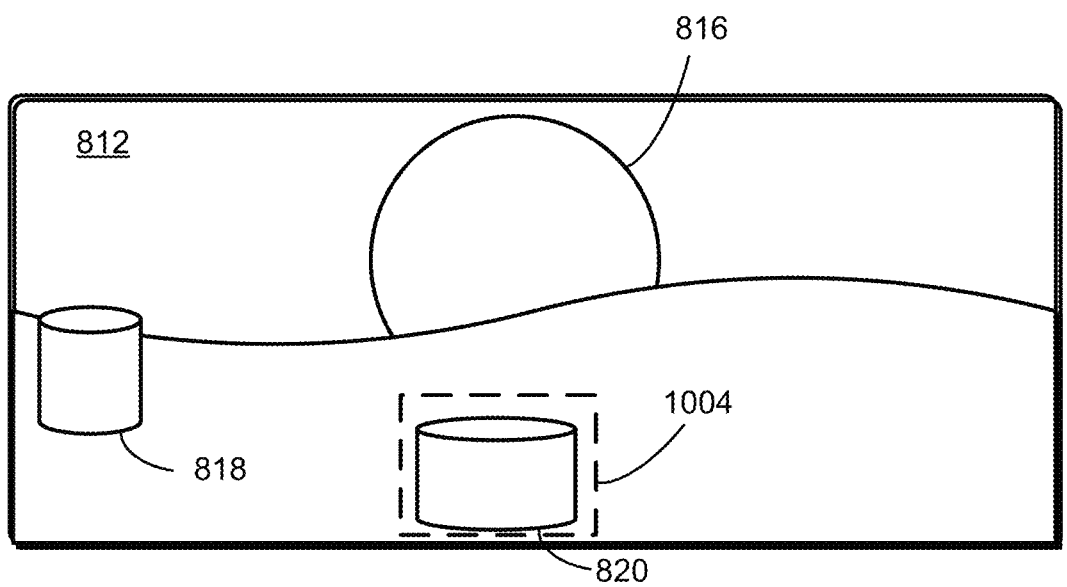

In continuing the present example, one or more values measured in the scenario depicted in FIG. 10E may be processed with the calibration data to determine that the user is looking at the second rendered object 820. In such an example, the one or more measured values shown in FIG. 10E may be processed with the calibration data to determine that the user is looking at a third section 1004 of the hardware display surface 802 in FIG. 10F.

In some examples, the device 800 may utilize data from a combination of resources to determine if a user is looking at the second rendered object 820 through the hardware display surface 802. As summarized above, a camera or other type of sensor 804 (FIG. 8A) mounted to the device 800 may be directed towards a user's field of view. Image data generated from the camera may be analyzed to determine if an object in the field of view is in a pre-determined position of an image of the image data. If an object is positioned within a pre-determined area of an image, such as the center of the image, a device may determine a gaze target by processing such data with eye position data. Such data may be utilized to supplement other types of data, such as position data from a GPS and/or data generated from a compass or accelerometer, to assist device 800 to determine a gaze direction, e.g., left, right, up, or down, and/or a gaze target.

Figure 11:
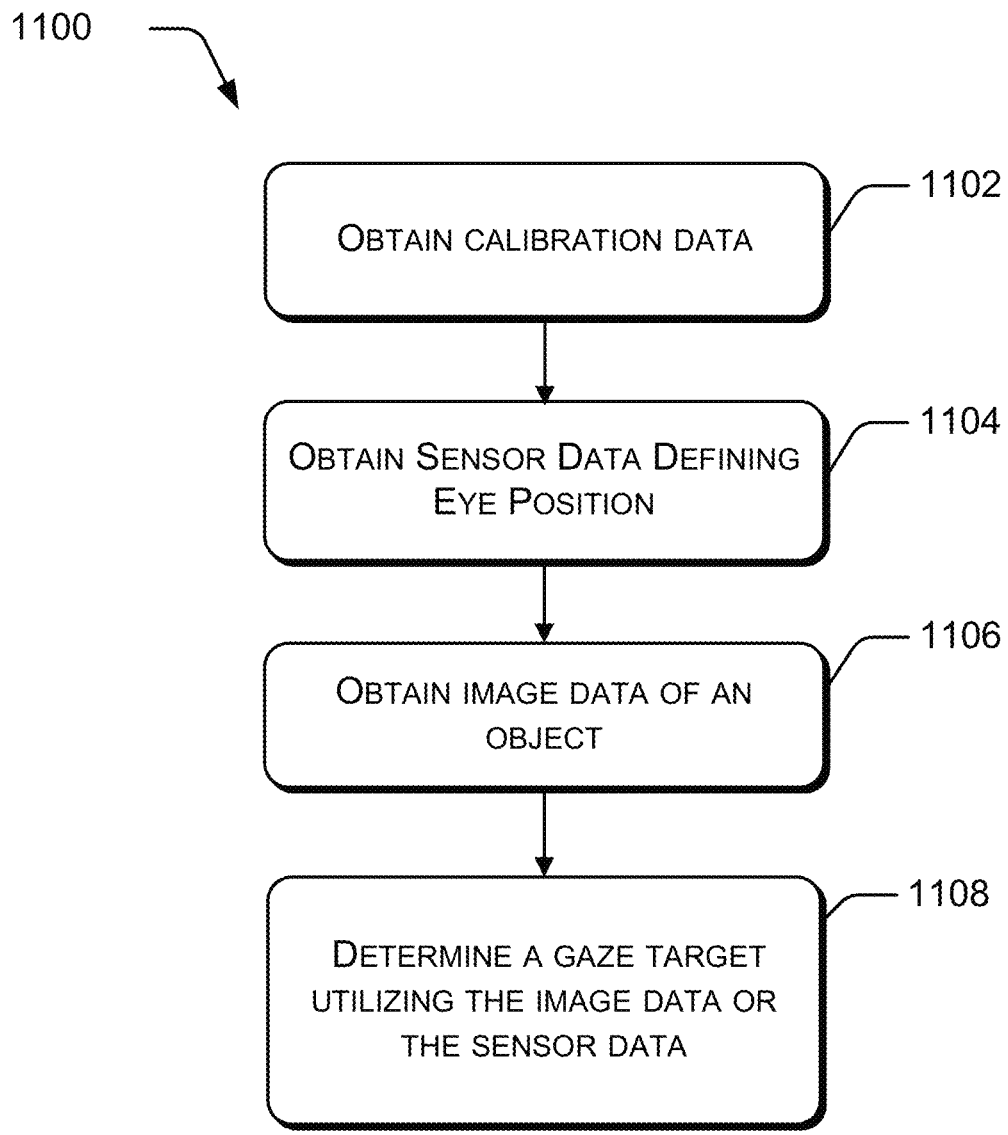
FIG. 11 is a flowchart illustrating aspects of an example process for determining a gaze target from gaze tracking data.

FIG. 11 is a flowchart illustrating aspects of an example process 1100 for determining a gaze target. In FIG. 11, the operations are described in the context of device 800 for convenience. However, the operations are applicable to other devices as well including, but not limited to, HMD device 112, HMD device 404, HMD device 408, or electronic device 706.

Block 1102 illustrates obtaining calibration data. In at least one example, an operating system, an application, or another module, may obtain calibration data. The calibration data may be stored in a data structure in a computer readable storage medium for access at a later time. The calibration data may be generated by the device 800 or the calibration data may be received from a remote resource. In some examples, sensors of computing device 800 may be positioned to track the position of at least one eye of a user. The sensors may cause the generation of one or more values that correlate the position of at least one eye of a user with a particular section or position of a hardware display surface. Such examples may utilize an initialization process where the device 800 displays one or more graphical elements at pre-determined locations. During the display of the one or more graphical elements, one or more inputs from a user may indicate that they are looking at the one or more graphical elements. In response to the input, the device 800 may generate calibration data comprising the values that correlate the position of at least one eye of a user with data identifying a particular position or section of a hardware display surface.

Block 1104 illustrates obtaining sensor data indicating the position of at least one eye of the user. In at least one example, an operating system, an application, or another module, may obtain sensor data from one or more sensors. The sensor data may be stored in a data structure in a sensor data collection module(s) or elsewhere in a computer-readable storage medium for access at a later time. As summarized above, sensor(s) directed toward at least one eye of the user may cause the generation of sensor data (e.g., gaze tracking data) indicating the position of at least one eye of the user. The sensor data may be processed to generate data indicating a gaze direction of a user. As will be described below, the data indicating the gaze direction of the user may be processed with the calibration data to determine if the user is looking at a gaze target, which may include a rendered object displayed on a hardware display surface.

Block 1106 illustrates obtaining image data of an object. In at least one example, an operating system, an application, or another module associated with a computer-readable media, may obtain sensor data. The image data or other information about the object may be stored in a data structure in a sensor data collection module(s), or elsewhere in any computer readable storage medium for access at a later time. In some examples, a camera or other type of sensor mounted to or otherwise in communication with the computing device 800 may be directed towards a user's field of view. The camera or other type of sensor may cause the generation of image data, which may include one or more images of an object that is in the user's field of view. The image data may be in any suitable format and generated by any suitable sensor, which may include the use of a depth map sensor, camera, etc.

Block 1108 illustrates determining a gaze target utilizing the image data or the sensor data. In at least one example, an operating system, an application, or another module associated with a computer-readable media, may determine the gaze target. For instance, if the user is looking at a real-world view of the object through a hardware display surface 802, and the sensor directed towards the user's field of view may generate image data of the real-world object. The image data may be analyzed to determine if the object in the field of view is in a pre-determined position of an image of the image data. For example, if an object is positioned within a pre-determined area of an image, such as the center of the image, the computing device 800 may determine that the object is a gaze target. In another example, sensor data (e.g., gaze tracking data) indicating the position of at least one eye of the user may be processed with the calibration data and/or image data to determine if the user is looking at a rendered object displayed on the hardware display surface. Such an example may be used to determine that the rendered object displayed on a hardware display surface is a gaze target.

Figure 12:
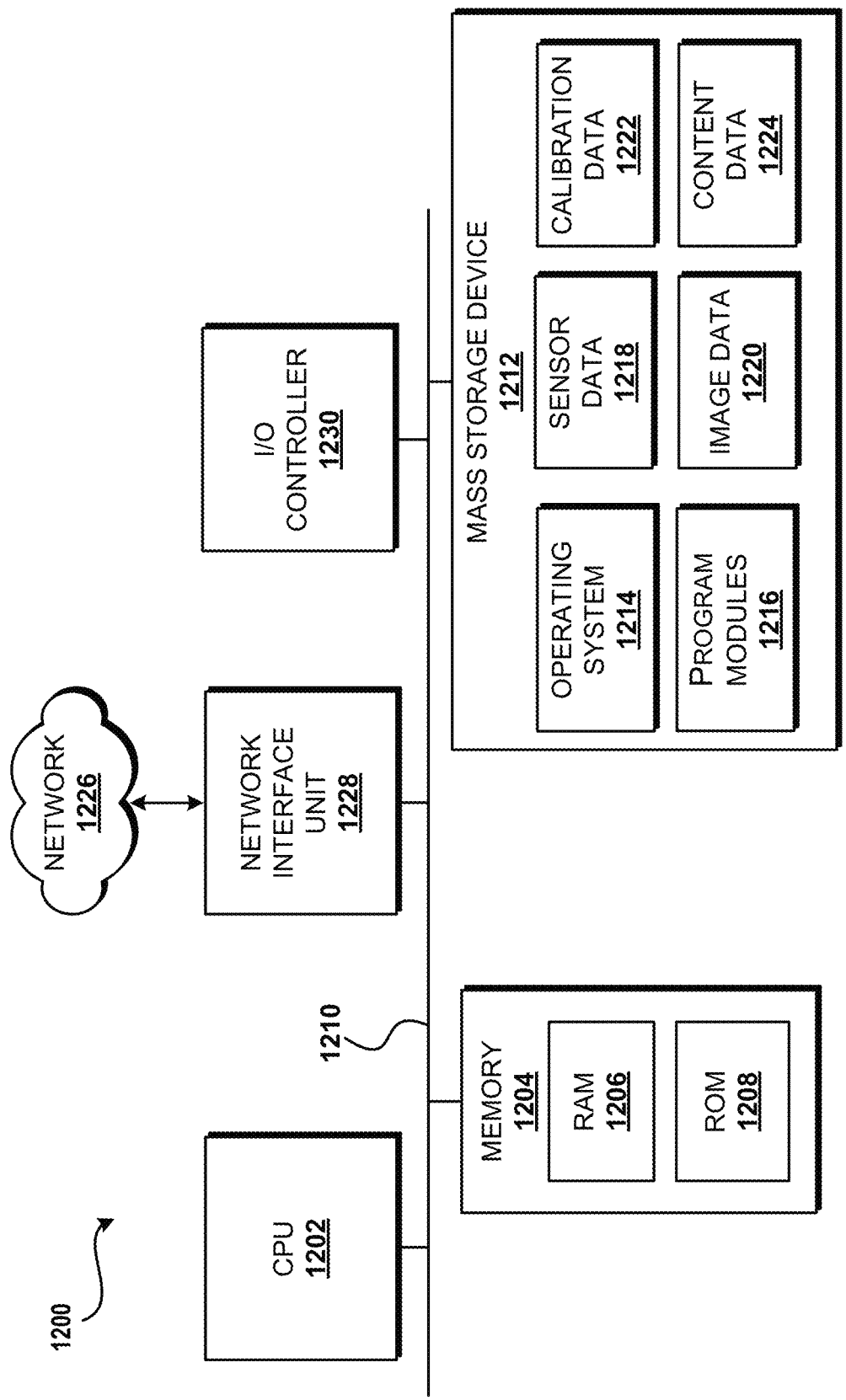
FIG. 12 is a schematic diagram illustrating an example computer architecture usable to implement aspects of identifying objects using gaze-tracking techniques.

FIG. 12 shows additional details of an example computer architecture 1200 for a computer, such as HMD device 112, mobile computing device 116, HMD device 404, HMD device 408, computing device 702, and/or electronic device 706, capable of executing the program components described above for recording or sharing data based on detected emotional or cognitive states of a user. Thus, the computer architecture 1200 illustrated in FIG. 12 illustrates an architecture for a server computer, mobile phone, a PDA, a smart phone, a desktop computer, a netbook computer, a tablet computer, a laptop computer, and/or a wearable computer. The computer architecture 1200 is an example architecture that may be used to execute, in whole or in part, aspects of the software components presented herein.

The computer architecture 1200 illustrated in FIG. 12 includes a central processing unit 1202 ("CPU"), a system memory 1204, including a random access memory 1206 ("RAM") and a read-only memory ("ROM") 1208, and a system bus 1210 that couples the memory 1204 to the CPU 1202. A basic input/output system ("BIOS") containing the basic routines that help to transfer information between elements within the computer architecture 1200, such as during startup, is stored in the ROM 1208. The computer architecture 1200 further includes a mass storage device 1212 for storing an operating system 1214, programs, module(s) 1216 (e.g., the emotional/cognitive state-triggered recording system 102 of FIG. 1 and FIG. 2, the emotional/cognitive state presentation system 402 of FIG. 4 and FIG. 5, modules 204, 206, and 208 of FIG. 2, modules 502, 506, 508 and 510 of FIG. 5, and modules 714, 716, 718, 720, 728, 752, 754, 756, and/or 758 of FIG. 7). Additionally, and/or alternatively, the mass storage device 1212 may store sensor data 1218, image data 1220 (e.g., photographs, computer generated images, object information about real and/or virtual objects in a scene, metadata about any of the foregoing, etc.), calibration data 1222, content data 1224 (e.g., computer generated images, videos, scenes, etc.), and the like, as described herein.

The mass storage device 1212 is connected to the CPU 1202 through a mass storage controller (not shown) connected to the bus 1210. The mass storage device 1212 and its associated computer-readable media provide non-volatile storage for the computer architecture 1200. Mass storage device 1212, memory 1204, computer-readable storage media 712, and computer-readable storage media 738 are examples of computer-readable media according to this disclosure. Although the description of computer-readable media contained herein refers to a mass storage device, such as a solid state drive, a hard disk or CD-ROM drive, it should be appreciated by those skilled in the art that computer-readable media may be any available computer storage media or communication media that may be accessed by the computer architecture 1200.

Communication media includes computer readable instructions, data structures, program modules, or other data in a modulated data signal such as a carrier wave or other transport mechanism and includes any delivery media. The term "modulated data signal" means a signal that has one or more of its characteristics changed or set in a manner as to encode information in the signal. By way of example, and not limitation, communication media includes wired media such as a wired network or direct-wired connection, and wireless media such as acoustic, RF, infrared and other wireless media. Combinations of any of the above should also be included within the scope of communication media.

By way of example, and not limitation, computer storage media may include volatile and non-volatile, removable and non-removable media implemented in any method or technology for storage of information such as computer-readable instructions, data structures, program modules or other data. For example, computer storage media includes, but is not limited to, RAM, ROM, erasable programmable read-only memory ("EPROM"), electrically erasable programmable read-only memory ("EEPROM"), flash memory or other solid state memory technology, compact disc read-only memory ("CD-ROM"), digital versatile disks ("DVD"), high definition/density digital versatile/video disc ("HD-DVD"), BLU-RAY disc, or other optical storage, magnetic cassettes, magnetic tape, magnetic disk storage or other magnetic storage devices, or any other medium which may be used to store the desired information and which may be accessed by the computer architecture 1200. For purposes of the claims, the phrase "computer storage medium," "computer-readable storage medium," and variations thereof, does not include communication media.

According to various configurations, the computer architecture 1200 may operate in a networked environment using logical connections to remote computers through the network 1226 and/or another network (not shown). The computer architecture 1200 may connect to the network 1226 through a network interface unit 1228 connected to the bus 1210. It should be appreciated that the network interface unit 1228 also may be utilized to connect to other types of networks and remote computer systems. The computer architecture 1200 also may include an input/output controller 1230 for receiving and processing input from input device(s) or input interface(s), and to provide output to an output device or output interface.

It should be appreciated that the software components described herein may, when loaded into the CPU 1202 and executed, transform the CPU 1202 and the overall computer architecture 1200 from a general-purpose computing system into a special-purpose computing system customized to facilitate the functionality presented herein. The CPU 1202 may be constructed from any number of transistors or other discrete circuit elements, which may individually or collectively assume any number of states. More specifically, the CPU 1202 may operate as a finite-state machine, in response to executable instructions contained within the software modules described herein. These computer-executable instructions may transform the CPU 1202 by specifying how the CPU 1202 transitions between states, thereby transforming the transistors or other discrete hardware elements constituting the CPU 1202. In some examples, processor(s) 710 and/or processor(s) 742 may correspond to CPU 1202.

Encoding the software modules presented herein also may transform the physical structure of the computer-readable media presented herein. The specific transformation of physical structure may depend on various factors, in different implementations of this description. Examples of such factors may include, but are not limited to, the technology used to implement the computer-readable media, whether the computer-readable media is characterized as primary or secondary storage, and the like. For example, if the computer-readable media is implemented as semiconductor-based memory, the software described herein may be encoded on the computer-readable media by transforming the physical state of the semiconductor memory. For example, the software may transform the state of transistors, capacitors, or other discrete circuit elements constituting the semiconductor memory. The software also may transform the physical state of such components in order to store data thereupon.

As another example, the computer-readable media described herein may be implemented using magnetic or optical technology. In such implementations, the software presented herein may transform the physical state of magnetic or optical media, when the software is encoded therein. These transformations may include altering the magnetic characteristics of particular locations within given magnetic media. These transformations also may include altering the physical features or characteristics of particular locations within given optical media, to change the optical characteristics of those locations. Other transformations of physical media are possible without departing from the scope and spirit of the present description, with the foregoing examples provided only to facilitate this discussion.

In light of the above, it should be appreciated that many types of physical transformations take place in the computer architecture 1200 in order to store and execute the software components presented herein. It also should be appreciated that the computer architecture 1200 may include other types of computing entities, including hand-held computers, embedded computer systems, personal digital assistants, and other types of computing entities known to those skilled in the art. It is also contemplated that the computer architecture 1700 may not include all of the components shown in FIG. 12, may include other components that are not explicitly shown in FIG. 12, or may utilize an architecture completely different than that shown in FIG. 12.

Figure 13:
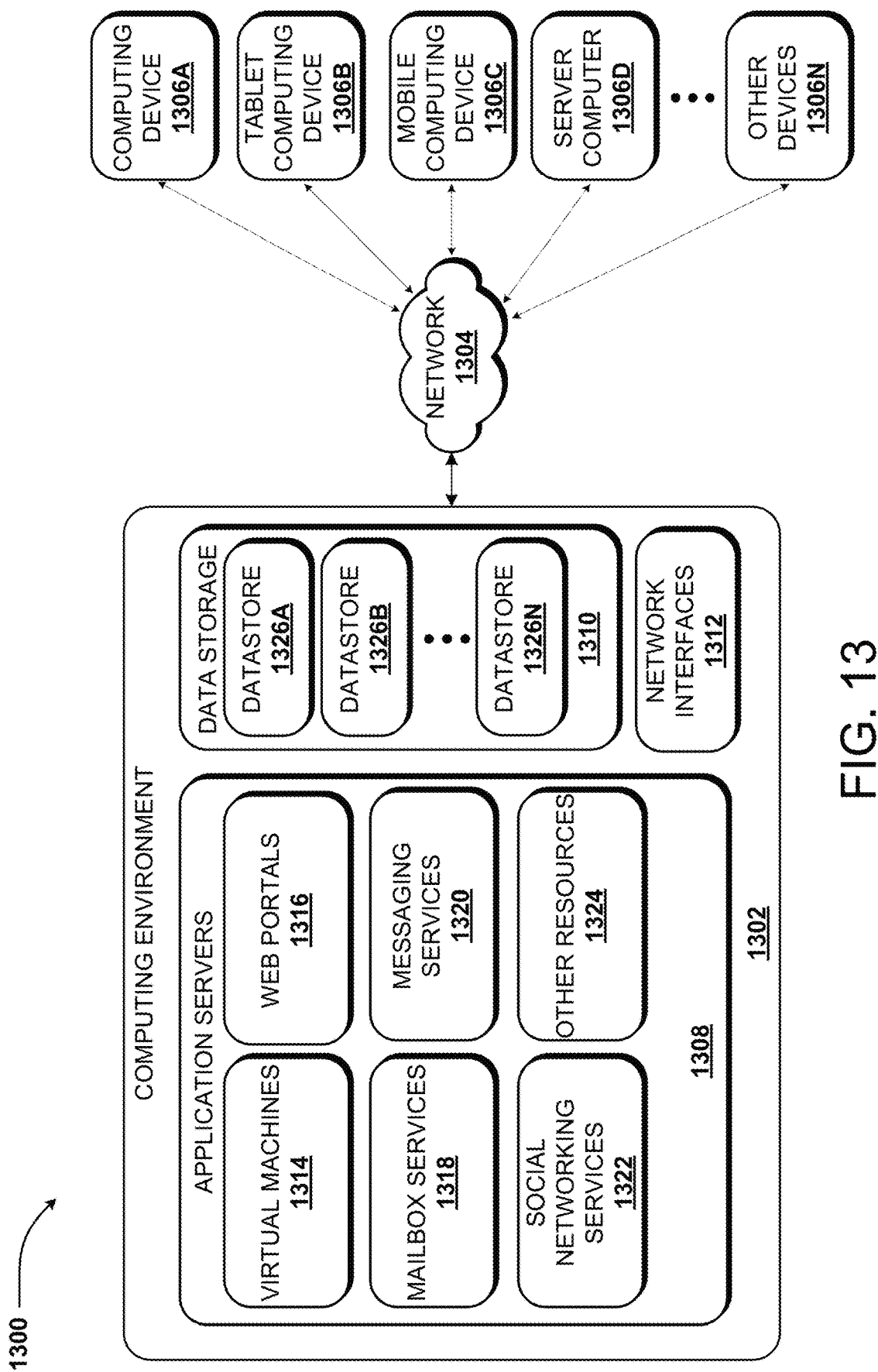
FIG. 13 is a schematic diagram illustrating an example distributed computing environment capable of implementing aspects of identifying objects using gaze-tracking techniques.

FIG. 13 depicts an example distributed computing environment 1300 capable of executing the software components described herein for implementing the identification of objects using gaze tracking techniques. Thus, the distributed computing environment 1300 illustrated in FIG. 13 may be utilized to execute any aspects of the software components presented herein to achieve aspects of the techniques described herein.

According to various implementations, the distributed computing environment 1300 includes a computing environment 1302 operating on, in communication with, or as part of a network 1304. In at least one example, at least some of computing environment 1300 may correspond to the HMD device 112, mobile computing device 116, HMD device 404, HMD device 408, computing device 702, and/or electronic device 706. The network 1304 may be or may include network(s) 120 and 704 described above with reference to FIG. 1 and FIG. 7. The network 1304 also may include various access networks. One or more client devices 1306A-1306N (hereinafter referred to collectively and/or generically as "clients 1306") may communicate with the computing environment 1302 via the network 1304 and/or other connections (not illustrated in FIG. 13). By way of example, HMD device 112, mobile computing device 116, HMD device 404, HMD device 408, and/or electronic device 706 may correspond to one or more of client devices 1306A-1306Q (collectively referred to as "clients 1306"), where Q may be any integer greater than or equal to 1 depending on the desired architecture. In one illustrated configuration, the clients 1306 include a computing device 1306A such as a laptop computer, a desktop computer, or other computing device, a slate or tablet computing device ("tablet computing device") 1306B, a mobile computing device 1306C such as a mobile telephone, a smart phone, or other mobile computing device, a server computer 1306D, a wearable computer 1306E, and/or other devices 1306N. It should be understood that any number of clients 1306 may communicate with the computing environment 1302. Two example computing architectures for the clients 1306 are illustrated and described herein with reference to FIGS. 12 and 14. It should be understood that the illustrated clients 1306 and computing architectures illustrated and described herein are illustrative, and should not be construed as being limited in any way.

In the illustrated configuration, the computing environment 1302 includes application servers 1308, data storage 1310, and one or more network interfaces 1312. According to various implementations, the functionality of the application servers 1308 may be provided by one or more server computers that are executing as part of, or in communication with, the network 1304. In some examples, the computing environment 1302 may correspond to or be representative of the one or more computing devices 702 in FIG. 7, which are in communication with and accessible by the one or more computing devices 706 via the network(s) 704 and/or 1304.

In at least one example, the application servers 1308 may host various services, virtual machines, portals, and/or other resources. In the illustrated configuration, the application servers 1308 may host one or more virtual machines 1314 for executing applications or other functionality. According to various implementations, the virtual machines 1314 may execute one or more applications and/or software modules for implementing object identification using gaze tracking techniques. The application servers 1308 also host or provide access to one or more portals, link pages, Web sites, and/or other information ("Web portals") 1316. The Web portals 1316 may be used to communicate with one or more client computers. The application servers 1308 may include one or more mailbox services 1318.

According to various implementations, the application servers 1308 also include one or more mailbox messaging services 1320. The mailbox services 1318 and/or messaging services 1320 may include electronic mail ("email") services, various personal information management ("PIM") services (e.g., calendar services, contact management services, collaboration services, etc.), instant messaging services, chat services, forum services, and/or other communication services.

The application servers 1308 also may include one or more social networking services 1322. The social networking services 1322 may include various social networking services including, but not limited to, services for sharing or posting status updates, instant messages, links, photos, videos, and/or other information; services for commenting or displaying interest in articles, products, blogs, or other resources; and/or other services. In some configurations, the social networking services 1322 are provided by or include the FACEBOOK® social networking service, the LINKEDIN® professional networking service, the MYSPACE® social networking service, the FOURSQUARE® geographic networking service, the YAMMER® office colleague networking service, and the like. In other configurations, the social networking services 1322 are provided by other services, sites, and/or providers that may or may not be explicitly known as social networking providers. For example, some web sites allow users to interact with one another via email, chat services, and/or other means during various activities and/or contexts such as reading published articles, commenting on goods or services, publishing, collaboration, gaming, and the like. Examples of such services include, but are not limited to, the WINDOWS LIVE® service and the XBOX LIVE® service from Microsoft Corporation in Redmond, Wash. Other services are possible and are contemplated.

The social networking services 1322 also may include commenting, blogging, and/or micro blogging services. Examples of such services include, but are not limited to, the YELP® commenting service, the KUDZU® review service, the OFFICETALK® enterprise micro blogging service, the TWITTER® messaging service, the GOOGLE BUZZ® service, and/or other services. It should be appreciated that the above lists of services are not exhaustive and that numerous additional and/or alternative social networking services 1322 are not mentioned herein for the sake of brevity. As such, the above configurations are illustrative, and should not be construed as being limited in any way. According to various implementations, the social networking services 1322 may host one or more applications and/or software modules for providing the functionality described herein for providing contextually-aware location sharing services for computing devices. For instance, any one of the application servers 1308 may communicate or facilitate the functionality and features described herein. For instance, a social networking application, mail client, messaging client, a browser running on a phone or any other client 1806 may communicate with a social networking service 1322.

As shown in FIG. 13, the application servers 1308 also may host other services, applications, portals, and/or other resources ("other resources") 1324. The other resources 1324 may deploy a service-oriented architecture or any other client-server management software. It thus may be appreciated that the computing environment 1302 may provide integration of the gaze-based object identification concepts and technologies described herein with various mailbox, messaging, social networking, and/or other services or resources.

As mentioned above, the computing environment 1302 may include the data storage 1310. According to various implementations, the functionality of the data storage 1310 is provided by one or more databases operating on, or in communication with, the network 1304. The functionality of the data storage 1310 also may be provided by one or more server computers configured to host data for the computing environment 1302. The data storage 1310 may include, host, or provide one or more real or virtual containers 1326A-1326N (referred to collectively and/or generically as "containers 1326"). Although not illustrated in FIG. 13, the containers 1326 also may host or store data structures and/or algorithms for execution by one or more modules of remote computing devices (e.g., emotional/cognitive state-triggered recording system 102 of FIG. 1 and FIG. 2, modules 204, 206, and/or 208 of FIG. 2, emotional/cognitive state presentation system 402 of FIGS. 4 and 5, modules 502, 506, 508, 510, and 512 of FIG. 5, and/or modules 714, 716, 718, 720, 752, 754, 756, 758, of FIG. 7). Aspects of the containers 1326 may be associated with a database program, file system and/or any program that stores data with secure access features. Aspects of the containers 1326 may also be implemented using products or services, such as ACTIVE DIRECTORY®, DKM®, ONEDRIVE®, DROPBOX® or GOOGLEDRIVE®.

The computing environment 1302 may communicate with, or be accessed by, the network interfaces 1312. The network interfaces 1312 may include various types of network hardware and software for supporting communications between two or more computing entities including, but not limited to, the clients 1306 and the application servers 1308. It should be appreciated that the network interfaces 1312 also may be utilized to connect to other types of networks and/or computer systems.

It should be understood that the distributed computing environment 1300 described herein may provide any aspects of the software elements described herein with any number of virtual computing resources and/or other distributed computing functionality that may be configured to execute any aspects of the software components described herein. According to various implementations of the concepts and technologies described herein, the distributed computing environment 1300 provides the software functionality described herein as a service to the clients 1306. It should be understood that the clients 1306 may include real or virtual machines including, but not limited to, server computers, web servers, personal computers, tablet computers, gaming consoles, smart televisions, mobile computing entities, smart phones, and/or other devices. As such, various configurations of the concepts and technologies described herein enable any device configured to access the distributed computing environment 1300 to utilize the functionality described herein for providing recording or sharing based on emotional or cognitive states of a user. In one specific example, as summarized above, techniques described herein may be implemented, at least in part, by a web browser application that may work in conjunction with the application servers 1308 of FIG. 13.

Figure 14:
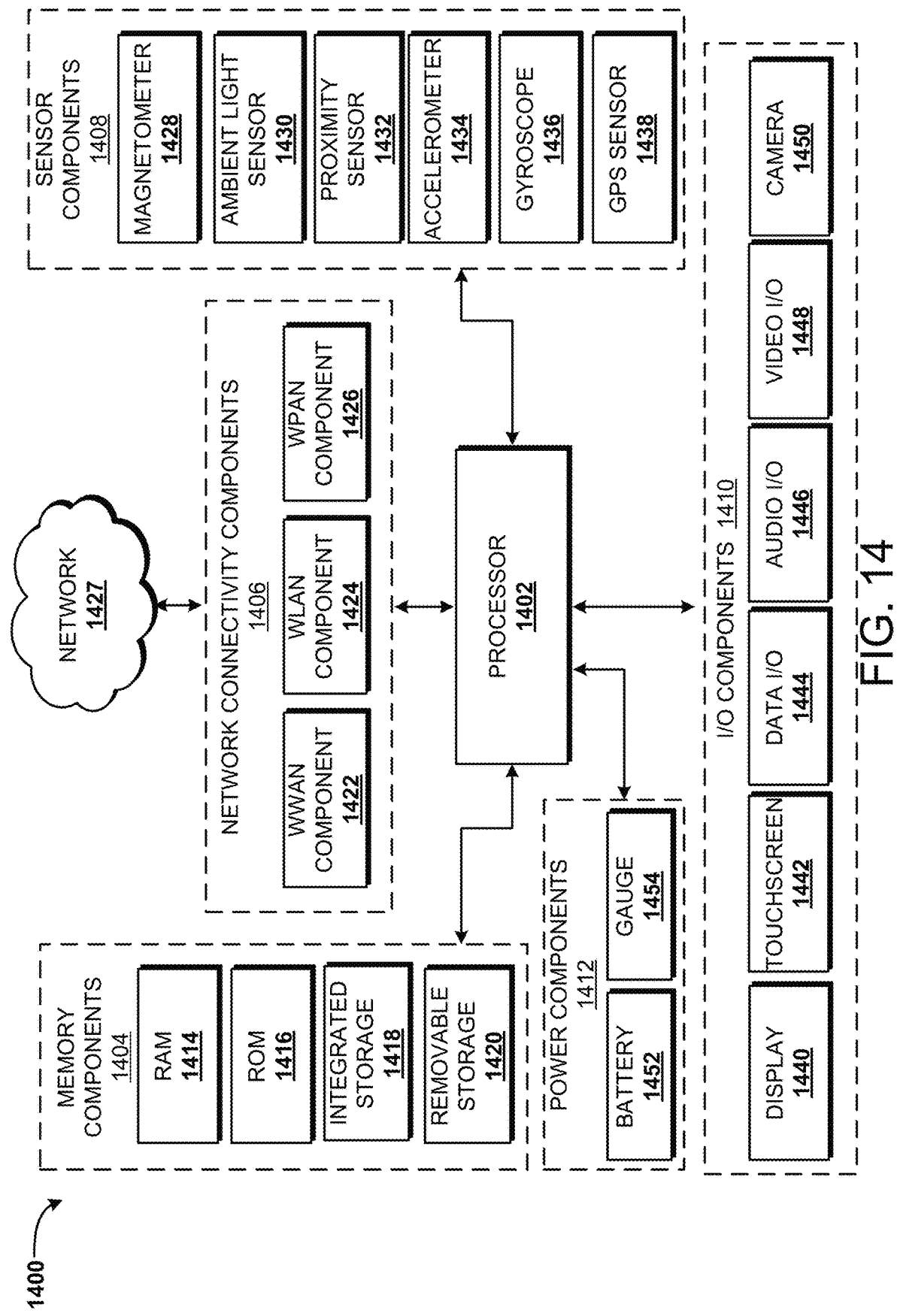
FIG. 14 is a schematic diagram illustrating another example computing device architecture usable to implement aspects of identifying objects using gaze-tracking techniques.

FIG. 14 is an illustrative computing device architecture 1400 for a computing device that is capable of executing various software components described which, in some examples, is usable to implement aspects of emotional/cognitive state-triggered recording or emotional/cognitive state presentation. The computing device architecture 1400 is applicable to computing entities that facilitate mobile computing due, in part, to form factor, wireless connectivity, and/or battery-powered operation. In some configurations, the computing entities include, but are not limited to, mobile telephones, tablet devices, slate devices, wearable devices, portable video game devices, and the like. Moreover, aspects of the computing device architecture 1400 may be applicable to traditional desktop computers, portable computers (e.g., laptops, notebooks, ultra-portables, and netbooks), server computers, and other computer systems. By way of example and not limitation, the computing device architecture 1400 is applicable to any of the clients shown in FIGS. 1, 4, 7, 12, and 13.

The computing device architecture 1400 illustrated in FIG. 14 includes a processor 1402, memory components 1404, network connectivity components 1406, sensor components 1408, input/output components 1410, and power components 1412. In the illustrated configuration, the processor 1402 is in communication with the memory components 1404, the network connectivity components 1406, the sensor components 1408, the input/output ("I/O") components 1410, and the power components 1412. Although no connections are shown between the individual components illustrated in FIG. 14, the components may interact to carry out device functions. In some configurations, the components are arranged so as to communicate via one or more busses (not shown).

The processor 1402 includes a central processing unit ("CPU") configured to process data, execute computer-executable instructions of one or more application programs, and communicate with other components of the computing device architecture 1400 in order to perform various functionality described herein. The processor 1402 may be utilized to execute aspects of the software components presented herein. In some examples, the processor 1402 may correspond to processor(s) 710, 742, and/or CPU 1202, as described above in reference to FIGS. 7 and 12.

In some configurations, the processor 1402 includes a graphics processing unit ("GPU") configured to accelerate operations performed by the CPU, including, but not limited to, operations performed by executing general-purpose scientific and/or engineering computing applications, as well as graphics-intensive computing applications such as high resolution video (e.g., 1080i, 1080p, and higher resolution), video games, three-dimensional ("3D") modeling applications, and the like. In some configurations, the processor 1402 is configured to communicate with a discrete GPU (not shown). In some examples, the processor 1402 may additionally or alternatively comprise a holographic processing unit (HPU) which is designed specifically to process and integrate data from multiple sensors of a head mounted computing device and to handle tasks such as spatial mapping, gesture recognition, and voice and speech recognition. In any case, the CPU, GPU, and/or HPU may be configured in accordance with a co-processing CPU/GPU/HPU computing model, wherein processing tasks are divided between the CPU, GPU, and/or HPU according to their respective strengths. For instance, the sequential part of an application may execute on the CPU, the computationally-intensive part is accelerated by the GPU, and certain specialized functions (e.g., spatial mapping, gesture recognition, and voice and speech recognition) may executed by an HPU.

In some configurations, the processor 1402 is, or is included in, a System-on-Chip ("SoC") along with one or more of the other components described herein below. For example, the SoC may include the processor 1402, a GPU, one or more of the network connectivity components 1406, and one or more of the sensor components 1408. In some configurations, the processor 1402 is fabricated, in part, utilizing a Package-on-Package ("PoP") integrated circuit packaging technique. The processor 1402 may be a single core or multi-core processor.

The processor 1402 may be created in accordance with an ARM architecture, available for license from ARM HOLDINGS of Cambridge, United Kingdom. Alternatively, the processor 1402 may be created in accordance with an x86 architecture, such as is available from INTEL CORPORATION of Mountain View, Calif. and others. In some configurations, the processor 1402 is a SNAPDRAGON SoC, available from QUALCOMM of San Diego, Calif., a TEGRA SoC, available from NVIDIA of Santa Clara, Calif., a HUMMINGBIRD SoC, available from SAMSUNG of Seoul, South Korea, an Open Multimedia Application Platform ("OMAP") SoC, available from TEXAS INSTRUMENTS of Dallas, Tex., a customized version of any of the above SoCs, or a proprietary SoC.

The memory components 1404 include a random access memory ("RAM") 1414, a read-only memory ("ROM") 1416, an integrated storage memory ("integrated storage") 1418, and a removable storage memory ("removable storage") 1420. In some configurations, the RAM 1414 or a portion thereof, the ROM 1416 or a portion thereof, and/or some combination the RAM 1414 and the ROM 1416 is integrated in the processor 1402. In some configurations, the ROM 1416 is configured to store a firmware, an operating system or a portion thereof (e.g., operating system kernel), and/or a bootloader to load an operating system kernel from the integrated storage 1418 and/or the removable storage 1420. In some examples, memory components 1404 may correspond to computer-readable storage media 712, computer-readable storage media 738, and/or memory 1204, as described above in reference to FIGS. 7 and 12, respectively.

The integrated storage 1418 may include a solid-state memory, a hard disk, or a combination of solid-state memory and a hard disk. The integrated storage 1418 may be soldered or otherwise connected to a logic board upon which the processor 1402 and other components described herein also may be connected. As such, the integrated storage 1418 is integrated in the computing device. The integrated storage 1418 is configured to store an operating system or portions thereof, application programs, data, and other software components described herein.

The removable storage 1420 may include a solid-state memory, a hard disk, or a combination of solid-state memory and a hard disk. In some configurations, the removable storage 1420 is provided in lieu of the integrated storage 1418. In other configurations, the removable storage 1420 is provided as additional optional storage. In some configurations, the removable storage 1420 is logically combined with the integrated storage 1418 such that the total available storage is made available as a total combined storage capacity. In some configurations, the total combined capacity of the integrated storage 1418 and the removable storage 1420 is shown to a user instead of separate storage capacities for the integrated storage 1418 and the removable storage 1420.

The removable storage 1420 is configured to be inserted into a removable storage memory slot (not shown) or other mechanism by which the removable storage 1420 is inserted and secured to facilitate a connection over which the removable storage 1420 may communicate with other components of the computing device, such as the processor 1402. The removable storage 1420 may be embodied in various memory card formats including, but not limited to, PC card, CompactFlash card, memory stick, secure digital ("SD"), miniSD, microSD, universal integrated circuit card ("UICC") (e.g., a subscriber identity module ("SIM") or universal SIM ("USIM")), a proprietary format, or the like.

It may be understood that one or more of the memory components 1404 may store an operating system. According to various configurations, the operating system includes, but is not limited to, SYMBIAN OS from SYMBIAN LIMITED, WINDOWS MOBILE OS from Microsoft Corporation of Redmond, Wash., WINDOWS PHONE OS from Microsoft Corporation, WINDOWS from Microsoft Corporation, PALM WEBOS from Hewlett-Packard Company of Palo Alto, Calif., BLACKBERRY OS from Research In Motion Limited of Waterloo, Ontario, Canada, IOS from Apple Inc. of Cupertino, Calif., and ANDROID OS from Google Inc. of Mountain View, Calif. Other operating systems are also contemplated.

The network connectivity components 1406 include a wireless wide area network component ("WWAN component") 1422, a wireless local area network component ("WLAN component") 1424, and a wireless personal area network component ("WPAN component") 1426. The network connectivity components 1406 facilitate communications to and from the network 1427 or another network, which may be a WWAN, a WLAN, or a WPAN. Although only the network 1427 is illustrated, the network connectivity components 1406 may facilitate simultaneous communication with multiple networks, including the network 1427 of FIG. 14. For example, the network connectivity components 1406 may facilitate simultaneous communications with multiple networks via one or more of a WWAN, a WLAN, or a WPAN. In some examples, the network 1427 may correspond to all or part of network(s) 120, network 704, network 1226, and/or network 1304, as shown in FIGS. 1, 7, 12, and 13.

The network 1427 may be or may include a WWAN, such as a mobile telecommunications network utilizing one or more mobile telecommunications technologies to provide voice and/or data services to a computing device utilizing the computing device architecture 1400 via the WWAN component 1422. The mobile telecommunications technologies may include, but are not limited to, Global System for Mobile communications ("GSM"), Code Division Multiple Access ("CDMA") ONE, CDMA2000, Universal Mobile Telecommunications System ("UMTS"), Long Term Evolution ("LTE"), and Worldwide Interoperability for Microwave Access ("WiMAX"). Moreover, the network 1427 may utilize various channel access methods (which may or cannot be used by the aforementioned standards) including, but not limited to, Time Division Multiple Access ("TDMA"), Frequency Division Multiple Access ("FDMA"), CDMA, wideband CDMA ("W-CDMA"), Orthogonal Frequency Division Multiplexing ("OFDM"), Space Division Multiple Access ("SDMA"), and the like. Data communications may be provided using General Packet Radio Service ("GPRS"), Enhanced Data rates for Global Evolution ("EDGE"), the High-Speed Packet Access ("HSPA") protocol family including High-Speed Downlink Packet Access ("HSDPA"), Enhanced Uplink ("EUL") or otherwise termed High-Speed Uplink Packet Access ("HSUPA"), Evolved HSPA ("HSPA+"), LTE, and various other current and future wireless data access standards. The network 1427 may be configured to provide voice and/or data communications with any combination of the above technologies. The network 1427 may be configured to or adapted to provide voice and/or data communications in accordance with future generation technologies.

In some configurations, the WWAN component 1422 is configured to provide dual-multi-mode connectivity to the network 1427. For example, the WWAN component 1422 may be configured to provide connectivity to the network 1427, wherein the network 1427 provides service via GSM and UMTS technologies, or via some other combination of technologies. Alternatively, multiple WWAN components 1422 may be utilized to perform such functionality, and/or provide additional functionality to support other non-compatible technologies (i.e., incapable of being supported by a single WWAN component). The WWAN component 1422 may facilitate similar connectivity to multiple networks (e.g., a UMTS network and an LTE network).

The network 1427 may be a WLAN operating in accordance with one or more Institute of Electrical and Electronic Engineers ("IEEE") 802.17 standards, such as IEEE 802.17a, 802.17b, 802.17g, 802.17n, and/or future 802.17 standard (referred to herein collectively as WI-FI). Draft 802.17 standards are also contemplated. In some configurations, the WLAN is implemented utilizing one or more wireless WI-FI access points. In some configurations, one or more of the wireless WI-FI access points are another computing device with connectivity to a WWAN that are functioning as a WI-FI hotspot. The WLAN component 1424 is configured to connect to the network 1427 via the WI-FI access points. Such connections may be secured via various encryption technologies including, but not limited to, WI-FI Protected Access ("WPA"), WPA2, Wired Equivalent Privacy ("WEP"), and the like.

The network 1427 may be a WPAN operating in accordance with Infrared Data Association ("IrDA"), BLUETOOTH, wireless Universal Serial Bus ("USB"), Z-Wave, ZIGBEE, or some other short-range wireless technology. In some configurations, the WPAN component 1426 is configured to facilitate communications with other devices, such as peripherals, computers, or other computing entities via the WPAN.

In at least one example, the sensor components 1408 may include a magnetometer 1428, an ambient light sensor 1430, a proximity sensor 1432, an accelerometer 1434, a gyroscope 1436, and a Global Positioning System sensor ("GPS sensor") 1438. It is contemplated that other sensors, such as, but not limited to, temperature sensors or shock detection sensors, strain sensors, moisture sensors also may be incorporated in the computing device architecture 1400.

The magnetometer 1428 is configured to measure the strength and direction of a magnetic field. In some configurations the magnetometer 1428 provides measurements to a compass application program stored within one of the memory components 1404 in order to provide a user with accurate directions in a frame of reference including the cardinal directions, north, south, east, and west. Similar measurements may be provided to a navigation application program that includes a compass component. Other uses of measurements obtained by the magnetometer 1428 are contemplated.

The ambient light sensor 1430 is configured to measure ambient light. In some configurations, the ambient light sensor 1430 provides measurements to an application program stored within one the memory components 1404 in order to automatically adjust the brightness of a display (described below) to compensate for low-light and high-light environments. Other uses of measurements obtained by the ambient light sensor 1430 are contemplated.

The proximity sensor 1432 is configured to detect the presence of an object or thing in proximity to the computing device without direct contact. In some configurations, the proximity sensor 1432 detects the presence of a user's body (e.g., the user's face) and provides this information to an application program stored within one of the memory components 1404 that utilizes the proximity information to enable or disable some functionality of the computing device. For example, a telephone application program may automatically disable a touchscreen (described below) in response to receiving the proximity information so that the user's face does not inadvertently end a call or enable/disable other functionality within the telephone application program during the call. Other uses of proximity as detected by the proximity sensor 1428 are contemplated.

The accelerometer 1434 is configured to measure proper acceleration. In some configurations, output from the accelerometer 1434 is used by an application program as an input mechanism to control some functionality of the application program. For example, the application program may be a video game in which a character, a portion thereof, or an object is moved or otherwise manipulated in response to input received via the accelerometer 1434. In some configurations, output from the accelerometer 1434 is provided to an application program for use in switching between landscape and portrait modes, calculating coordinate acceleration, or detecting a fall. Other uses of the accelerometer 1434 are contemplated.

The gyroscope 1436 is configured to measure and maintain orientation. In some configurations, output from the gyroscope 1436 is used by an application program as an input mechanism to control some functionality of the application program. For example, the gyroscope 1436 may be used for accurate recognition of movement within a 3D environment of a video game application or some other application. In some configurations, an application program utilizes output from the gyroscope 1436 and the accelerometer 1434 to enhance control of some functionality of the application program. Other uses of the gyroscope 1436 are contemplated.

The GPS sensor 1438 is configured to receive signals from GPS satellites for use in calculating a location. The location calculated by the GPS sensor 1438 may be used by any application program that requires or benefits from location information. For example, the location calculated by the GPS sensor 1438 may be used with a navigation application program to provide directions from the location to a destination or directions from the destination to the location. Moreover, the GPS sensor 1438 may be used to provide location information to an external location-based service, such as E1717 service. The GPS sensor 1438 may obtain location information generated via WI-FI, WIMAX, and/or cellular triangulation techniques utilizing one or more of the network connectivity components 1406 to aid the GPS sensor 1438 in obtaining a location fix. The GPS sensor 1438 may also be used in Assisted GPS ("A-GPS") systems.

In at least one example, the I/O components 1410 may correspond to the input/output devices 740, described above with reference to FIG. 12. Additionally, and/or alternatively, the I/O components may include a display 1440, a touchscreen 1442, a data I/O interface component ("data I/O") 1444, an audio I/O interface component ("audio I/O") 1446, a video I/O interface component ("video I/O") 1448, and a camera 1470. In some configurations, the display 1440 and the touchscreen 1442 are combined. In some configurations two or more of the data I/O component 1444, the audio I/O component 1446, and the video I/O component 1448 are combined. The I/O components 1410 may include discrete processors configured to support the various interface described below, or may include processing functionality built-in to the processor 1402.

The display 1440 is an output device configured to present information in a visual form. In particular, the display 1440 may present graphical user interface ("GUI") elements, text, images, video, notifications, virtual buttons, virtual keyboards, messaging data, Internet content, device status, time, date, calendar data, preferences, map information, location information, and any other information that is capable of being presented in a visual form. In some configurations, the display 1440 is a liquid crystal display ("LCD") utilizing any active or passive matrix technology and any backlighting technology (if used). In some configurations, the display 1440 is an organic light emitting diode ("OLED") display. In some configurations, the display 1440 is a holographic display. Other display types are contemplated.

In at least one example, the display 1440 may correspond to a hardware display surface of the computing device 112 and/or the electronic device 706. As described above, the hardware display surface may be configured to graphically associate holographic user interfaces and other graphical elements with an object seen through the hardware display surface or rendered objects displayed on the hardware display surface.

The touchscreen 1442, also referred to herein as a "touch-enabled screen," is an input device configured to detect the presence and location of a touch. The touchscreen 1442 may be a resistive touchscreen, a capacitive touchscreen, a surface acoustic wave touchscreen, an infrared touchscreen, an optical imaging touchscreen, a dispersive signal touchscreen, an acoustic pulse recognition touchscreen, or may utilize any other touchscreen technology. In some configurations, the touchscreen 1442 is incorporated on top of the display 1440 as a transparent layer to enable a user to use one or more touches to interact with objects or other information presented on the display 1440. In other configurations, the touchscreen 1442 is a touch pad incorporated on a surface of the computing device that does not include the display 1440. For example, the computing device may have a touchscreen incorporated on top of the display 1440 and a touch pad on a surface opposite the display 1440.

In some configurations, the touchscreen 1442 is a single-touch touchscreen. In other configurations, the touchscreen 1442 is a multi-touch touchscreen. In some configurations, the touchscreen 1442 is configured to detect discrete touches, single touch gestures, and/or multi-touch gestures. These are collectively referred to herein as gestures for convenience. Several gestures will now be described. It should be understood that these gestures are illustrative and are not intended to limit the scope of the appended claims. Moreover, the described gestures, additional gestures, and/or alternative gestures may be implemented in software for use with the touchscreen 1442. As such, a developer may create gestures that are specific to a particular application program.

In some configurations, the touchscreen 1442 supports a tap gesture in which a user taps the touchscreen 1442 once on an item presented on the display 1440. The tap gesture may be used to perform various functions including, but not limited to, opening or launching whatever the user taps. In some configurations, the touchscreen 1442 supports a double tap gesture in which a user taps the touchscreen 1442 twice on an item presented on the display 1440. The double tap gesture may be used to perform various functions including, but not limited to, zooming in or zooming out in stages. In some configurations, the touchscreen 1442 supports a tap and hold gesture in which a user taps the touchscreen 1442 and maintains contact for at least a predefined time. The tap and hold gesture may be used to perform various functions including, but not limited to, opening a context-specific menu.

In some configurations, the touchscreen 1442 supports a pan gesture in which a user places a finger on the touchscreen 1442 and maintains contact with the touchscreen 1442 while moving the finger on the touchscreen 1442. The pan gesture may be used to perform various functions including, but not limited to, moving through screens, images, or menus at a controlled rate. Multiple finger pan gestures are also contemplated. In some configurations, the touchscreen 1442 supports a flick gesture in which a user swipes a finger in the direction the user wants the screen to move. The flick gesture may be used to perform various functions including, but not limited to, scrolling horizontally or vertically through menus or pages. In some configurations, the touchscreen 1442 supports a pinch and stretch gesture in which a user makes a pinching motion with two fingers (e.g., thumb and forefinger) on the touchscreen 1442 or moves the two fingers apart. The pinch and stretch gesture may be used to perform various functions including, but not limited to, zooming gradually in or out of a website, map, or picture.

Although the above gestures have been described with reference to the use of one or more fingers for performing the gestures, other appendages such as toes or objects such as styluses may be used to interact with the touchscreen 1442. As such, the above gestures should be understood as being illustrative and should not be construed as being limited in any way.

The data I/O interface component 1444 is configured to facilitate input of data to the computing device and output of data from the computing device. In some configurations, the data I/O interface component 1444 includes a connector configured to provide wired connectivity between the computing device and a computer system, for example, for synchronization operation purposes. The connector may be a proprietary connector or a standardized connector such as USB, micro-USB, mini-USB, or the like. In some configurations, the connector is a dock connector for docking the computing device with another device such as a docking station, audio device (e.g., a digital music player), or video device.

The audio I/O interface component 1446 is configured to provide audio input and/or output capabilities to the computing device. In some configurations, the audio I/O interface component 1446 includes a microphone configured to collect audio signals. In some configurations, the audio I/O interface component 1446 includes a headphone jack configured to provide connectivity for headphones or other external speakers. In some configurations, the audio I/O interface component 1446 includes a speaker for the output of audio signals. In some configurations, the audio I/O interface component 1446 includes an optical audio cable out.

The video I/O interface component 1448 is configured to provide video input and/or output capabilities to the computing device. In some configurations, the video I/O interface component 1448 includes a video connector configured to receive video as input from another device (e.g., a video media player such as a DVD or BLURAY player) or send video as output to another device (e.g., a monitor, a television, or some other external display). In some configurations, the video I/O interface component 1448 includes a High-Definition Multimedia Interface ("HDMI"), mini-HDMI, micro-HDMI, DisplayPort, or proprietary connector to input/output video content. In some configurations, the video I/O interface component 1448 or portions thereof is combined with the audio I/O interface component 1446 or portions thereof.

The camera 1470 may be configured to capture still images and/or video. The camera 1470 may utilize a charge coupled device ("CCD") or a complementary metal oxide semiconductor ("CMOS") image sensor to capture images. In some configurations, the camera 1470 includes a flash to aid in taking pictures in low-light environments. Settings for the camera 1470 may be implemented as hardware or software buttons. Images and/or video captured by camera 1470 may additionally or alternatively be used to detect non-touch gestures, facial expressions, eye movement, or other movements and/or characteristics of the user.

Although not illustrated, one or more hardware buttons may also be included in the computing device architecture 1400. The hardware buttons may be used for controlling some operational aspect of the computing device. The hardware buttons may be dedicated buttons or multi-use buttons. The hardware buttons may be mechanical or sensor-based.

The illustrated power components 1412 include one or more batteries 1472, which may be connected to a battery gauge 1474. The batteries 1472 may be rechargeable or disposable. Rechargeable battery types include, but are not limited to, lithium polymer, lithium ion, nickel cadmium, and nickel metal hydride. Each of the batteries 1472 may be made of one or more cells.

The battery gauge 1474 may be configured to measure battery parameters such as current, voltage, and temperature. In some configurations, the battery gauge 1474 is configured to measure the effect of a battery's discharge rate, temperature, age and other factors to predict remaining life within a certain percentage of error. In some configurations, the battery gauge 1474 provides measurements to an application program that is configured to utilize the measurements to present useful power management data to a user. Power management data may include one or more of a percentage of battery used, a percentage of battery remaining, a battery condition, a remaining time, a remaining capacity (e.g., in watt hours), a current draw, and a voltage.

The power components 1412 may also include a power connector, which may be combined with one or more of the aforementioned I/O components 1410. The power components 1412 may interface with an external power system or charging equipment via a power I/O component.

Example Clauses

A. A method comprising: detecting, at a first device associated with a first user, a second device associated with a second user; determining, by the first device, an emotional or cognitive state of the first user; at least partly in response to detecting the trusted relationship, communicating to the second device, an indication of the emotional or cognitive state of the first user.

B. A method as paragraph A recites, wherein detecting the second device associated with the second user comprises detecting that the second device is in proximity to the first device.

C. A method as paragraph A or paragraph B recites, wherein detecting the second device associated with the second user comprises determining that a trusted relationship exists between the first user and the second user.

D. A method as any of paragraphs A-C recite, wherein determining the emotional or cognitive state of the first user comprises receiving biometric sensor data indicating the emotional or cognitive state of the first user.

E. A method as any of paragraphs A-D recite, further comprising: receiving from the second device, data identifying an emotional or cognitive state of the second user; presenting an indicator of the emotional or cognitive state of the second user.

F. A method as paragraph E recites, wherein presenting the indicator of the emotional or cognitive state of the second user includes presenting a virtual indicator within a virtual reality environment or mixed reality environment visible to the first user.

G. A method as paragraph F recites, wherein the virtual indicator includes a colored aura associated with the second user or a representation of the second user.

H. A system comprising: a device proximity detection module associated with a first device configured to detect a second device in proximity to the first device, wherein the first device is associated with a first user and the second device is associated with a second user; a sensor data analysis module associated with the first device, the sensor data analysis module configured to determine an emotional or cognitive state of the first user based at least in part on sensor data representing a physiological condition of the first user; and a communication interface configured to send, from the first device to the second device, data indicating the emotional or cognitive state of the first user.

I. A system as paragraph H recites, wherein the communication interface is further configured to receive at the first device, from the second device, data indicating an emotional or cognitive state of the second user.

J. A system as paragraph H or paragraph I recites, further comprising a presentation interface, wherein the presentation interface is configured to present the data indicating the emotional or cognitive state of the second user.

K A system as paragraph J recites, wherein the presentation interface comprises a display device configured to display an augmented reality view.

L. A system as any of paragraphs H-K recite, further comprises a biometric sensor to capture the sensor data.

M. A system as any of paragraphs H-L recite, wherein the analysis module is implemented as a digital neural network (DNN) chip.

N. A system as any of paragraphs H-M recite, implemented as a head-mounted display device.

O. One or more computer readable media having computer-executable instructions stored thereon, which, when executed by a first computing device, cause the first computing device to perform operations comprising: detecting a second computing device in proximity to the first computing device, wherein the first computing device is associated with a first user and the second computing device is associated with a second user; determining, based on sensor data, an emotional or cognitive state of the first user; and transmitting from the first computing device to the second device, data indicating the emotional or cognitive state of the first user.

P. One or more computer readable media as paragraph O recites, wherein detecting a second computing device in proximity to the first computing device further comprises determining a trusted relationship between the first user and the second user.

Q. One or more computer readable media as paragraph O or paragraph P recites, the operations further comprising: receiving at the first computing device, from the second computing device, data indicating an emotional or cognitive state of the second user; presenting, for the first user, an indication of the emotional or cognitive state of the second user.

R. One or more computer readable media as paragraph Q recites, wherein the indication of the emotional or cognitive state of the second user comprises a visual indication within an augmented reality view.

S. One or more computer readable media as any of paragraphs O-R recite, the operations further comprising capturing the sensor data using a biometric sensor.

T. One or more computer readable media as any of paragraphs O-S recite, implemented as a component of a head-mounted display device.

CONCLUSION

Although the techniques have been described in language specific to structural features and/or methodological acts, it is to be understood that the appended claims are not necessarily limited to the features or acts described. Rather, the features and acts are described as example implementations of such techniques.

The operations of the example processes are illustrated in individual blocks and summarized with reference to those blocks. The processes are illustrated as logical flows of blocks, each block of which can represent one or more operations that can be implemented in hardware, software, or a combination thereof. In the context of software, the operations represent computer-executable instructions stored on one or more computer-readable media that, when executed by one or more processors, enable the one or more processors to perform the recited operations. Generally, computer-executable instructions include routines, programs, objects, modules, components, data structures, and the like that perform particular functions or implement particular abstract data types. The order in which the operations are described is not intended to be construed as a limitation, and any number of the described operations can be executed in any order, combined in any order, subdivided into multiple sub-operations, and/or executed in parallel to implement the described processes. The described processes can be performed by resources associated with one or more devices 112, 116, 118, 404, 408, 702, and 706 such as one or more internal or external CPUs or GPUs, and/or one or more pieces of hardware logic such as FPGAs, DSPs, or other types of accelerators.

All of the methods and processes described above may be embodied in, and fully automated via, specialized computer hardware. Some or all of the methods may alternatively be embodied in software code modules executed by one or more general purpose computers or processors. The code modules may be stored in any type of computer-readable storage medium or other computer storage device.

Conditional language such as, among others, "can," "could," "might" or "may," unless specifically stated otherwise, are understood within the context to present that certain examples include, while other examples do not include, certain features, elements and/or steps. Thus, such conditional language is not generally intended to imply that certain features, elements and/or steps are in any way required for one or more examples or that one or more examples necessarily include logic for deciding, with or without user input or prompting, whether certain features, elements and/or steps are included or are to be performed in any particular example. Conjunctive language such as the phrase "at least one of X, Y or Z," unless specifically stated otherwise, is to be understood to present that an item, term, etc. may be either X, Y, or Z, or a combination thereof.

Any routine descriptions, elements or blocks in the flow diagrams described herein and/or depicted in the attached figures should be understood as potentially representing modules, segments, or portions of code that include one or more executable instructions for implementing specific logical functions or elements in the routine. Alternate implementations are included within the scope of the examples described herein in which elements or functions may be deleted, or executed out of order from that shown or discussed, including substantially synchronously or in reverse order, depending on the functionality involved as would be understood by those skilled in the art. It should be emphasized that many variations and modifications may be made to the above-described examples, the elements of which are to be understood as being among other acceptable examples. All such modifications and variations are intended to be included herein within the scope of this disclosure and protected by the following claims.

What is claimed is:
1. A method comprising:
 detecting, at a first device associated with a first user, a second device associated with a second user that is in viewing proximity to the first device;
 determining, by the first device, an emotional or cognitive state of the first user;

accessing a parameter, stored in association with the second user, to verify that the first user has previously selected the second user as a specific person with which the emotional or cognitive state of the first user can be shared;

at least partly in response to detecting the second device is in viewing proximity to the first device, communicating, to the second device, an indication of the emotional or cognitive state of the first user;

at least partly in response to detecting the second device is in viewing proximity to the first device, receiving, from the second device, an indication of an emotional or cognitive state of the second user; and presenting a virtual indicator of the emotional or cognitive state of the second user based on a position of the second user within a virtual reality environment or mixed reality environment visible to the first user.

2. A method as recited in claim 1, wherein determining the emotional or cognitive state of the first user comprises receiving biometric sensor data indicating the emotional or cognitive state of the first user.

3. A method as recited in claim 1, wherein the virtual indicator includes a colored aura selected to represent the emotional or cognitive state of the second user.

4. A method as recited in claim 1, wherein the parameter indicates the emotional or cognitive state of the first user as a specific emotional or cognitive state of the first user that is allowed to be shared with the second user.

5. A method as recited in claim 1, wherein determining the emotional or cognitive state of the first user is implemented after detecting the second device associated with the second user that is in viewing proximity to the first device.

6. A method as recited in claim 1, wherein the data indicating the emotional or cognitive state of the first user is sent and the indication of the emotional or cognitive state of the second user is received via a Bluetooth connection.

7. A device comprising:
one or more processors; and
computer readable media storing computer-executable instructions that, when executed by the one or more processors, cause the device to:
detect another device in viewing proximity to the device, wherein the device is associated with a first user and the other device is associated with a second user;
determine an emotional or cognitive state of the first user based at least in part on sensor data representing a physiological condition of the first user;
access a parameter, stored in association with the second user, to verify that the first user has previously selected the second user as a specific person with which the emotional or cognitive state of the first user can be shared;
send, from the device to the other device and based at least in part on the other device being in viewing proximity to the device, data indicating the emotional or cognitive state of the first user;
at least partly in response to detecting that the other device in viewing proximity to the device, receive, from the other device, an indication of an emotional or cognitive state of the second user; and
present a virtual indicator of the emotional or cognitive state of the second user based on a position of the second user within a virtual reality environment or mixed reality environment visible to the first user.

8. A device as recited in claim 7, wherein the computer-executable instructions further cause the device to present the virtual indicator around the second user via a display device.

9. A device as recited in claim 7, further comprising a biometric sensor to capture the sensor data.

10. A device as recited in claim 7, wherein the determining the emotional or cognitive state of the first user is implemented by a digital neural network (DNN) chip.

11. A device as recited in claim 7, implemented as a head-mounted display device.

12. A device as recited in claim 7, wherein the data indicating the emotional or cognitive state of the first user is sent and the indication of the emotional or cognitive state of the second user is received via a Bluetooth connection.

13. One or more non-transitory computer readable media having computer-executable instructions stored thereon, which, when executed by a first computing device, cause the first computing device to perform operations comprising:
detecting a second computing device in viewing proximity to the first computing device, wherein the first computing device is associated with a first user and the second computing device is associated with a second user;
determining, based on sensor data, an emotional or cognitive state of the first user;
accessing a parameter, stored in association with the second user, to verify that the first user has previously selected the second user as a specific person with which the emotional or cognitive state of the first user can be shared;
transmitting from the first computing device to the second computing device based at least in part on the second computing device being in viewing proximity to the first computing device, data indicating the emotional or cognitive state of the first user;
at least partly in response to detecting the second computing device in viewing proximity to the first computing device, receiving, from the second computing device, an indication of an emotional or cognitive state of the second user; and
presenting a virtual indicator of the emotional or cognitive state of the second user based on a position of the second user within a virtual reality environment or mixed reality environment visible to the first user.

14. One or more non-transitory computer readable media as recited in claim 13, wherein detecting the second computing device in proximity to the first computing device further comprises determining a trusted relationship exists between the first user and the second user.

15. One or more non-transitory computer readable media as recited in claim 13, the operations further comprising capturing the sensor data using a biometric sensor.

16. One or more non-transitory computer readable media as recited in claim 13, implemented as a component of a head-mounted display device.

17. One or more non-transitory computer readable media as recited in claim 13, wherein the parameter indicates the emotional or cognitive state of the first user as a specific emotional or cognitive state of the first user that is allowed to be shared with the second user.

18. One or more non-transitory computer readable media as recited in claim 13, wherein the data indicating the emotional or cognitive state of the first user is transmitted and the indication of the emotional or cognitive state of the second user is received via a Bluetooth connection.

\* \* \* \* \*